US012661278B2

(12) United States Patent
Wright et al.

(10) Patent No.: US 12,661,278 B2
(45) Date of Patent: *Jun. 23, 2026

(54) ABSORBENT COMPOSITE, AN ABSORBENT ARTICLE EMPLOYING THE SAME, AND METHODS, SYSTEMS, AND APPARATUS FOR MAKING THE ABSORBENT COMPOSITE AND/OR ARTICLE

(71) Applicant: DSG Technology Holdings Ltd., Kwai Chung (HK)

(72) Inventors: Andrew Wright, Rotherham (GB); Eugenio Varona, Marietta, GA (US); Anne Smid, Wolvega (NL); Dennis Smid, Wolvega (NL)

(73) Assignee: DSG Technology Holdings Ltd., Kwai Chung (HK)

( * ) Notice: Subject to any disclaimer, the term of this patent is extended or adjusted under 35 U.S.C. 154(b) by 166 days.

This patent is subject to a terminal disclaimer.

(21) Appl. No.: 17/372,664

(22) Filed: Jul. 12, 2021

(65) Prior Publication Data

US 2022/0104975 A1     Apr. 7, 2022

Related U.S. Application Data

(63) Continuation of application No. 16/206,764, filed on Nov. 30, 2018, now Pat. No. 11,090,203, which is a
(Continued)

(51) Int. Cl.
*A61F 13/535* (2006.01)
*A61F 13/15* (2006.01)
(Continued)

(52) U.S. Cl.
CPC ...... *A61F 13/535* (2013.01); *A61F 13/15203* (2013.01); *A61F 13/15658* (2013.01);
(Continued)

(58) Field of Classification Search
CPC .......... A61F 13/15203; A61F 13/15658; A61F 13/15699; A61F 13/49001; A61F 13/5323;
(Continued)

(56) References Cited

U.S. PATENT DOCUMENTS 3,071,138 A     1/1963  Garcia
3,670,731 A     6/1972  Harmon
(Continued)

FOREIGN PATENT DOCUMENTS

CA          2485743 A1     11/2003
CN          1177472 A       4/1998
(Continued)

OTHER PUBLICATIONS

1st Office Action from Canadian Application No. 2,643,482, dated Oct. 30, 2013; 3 pages.
(Continued)

*Primary Examiner* — Michele Kidwell
(74) *Attorney, Agent, or Firm* — Alberto Q. Amatong, Jr.; Amatong McCoy LLC

(57) ABSTRACT
An absorbent core composite is disclosed for incorporation into a disposable absorbent article. The composite includes a first material layer and a second material layer (preferably nonwoven) partially secured to the first material layer to define at least one pocket therebetween. Preferably, multiple pockets are defined, except in the case of where a generally uniform layer or bed of absorbent is preferred or better suited for the application. The pocket is said have a fixed initial volume. Further, an aggregate of absorbent particles is provided in the pocket(s) to occupy a portion of the fixed initial volume. The absorbent particles are preferably SAP particles and is characterized by a dry volume associated with a dry state and a swell volume associated with a liquid
(Continued)

saturation state. In respect to or for the pocket, the aggregate is characterized by a collective dry volume and a collective swell volume, wherein the pocket has an initial configuration that retains the aggregate therein.

19 Claims, 16 Drawing Sheets

Related U.S. Application Data continuation of application No. 14/321,773, filed on Jul. 1, 2014, now Pat. No. 10,201,462.

(60) Provisional application No. 61/842,961, filed on Jul. 3, 2013, provisional application No. 61/843,986, filed on Jul. 9, 2013.

(51) Int. Cl.

| | |
|---|---|
| *A61F 13/49* | (2006.01) |
| *A61F 13/53* | (2006.01) |
| *A61F 13/532* | (2006.01) |
| *A61F 13/537* | (2006.01) |
| *A61F 13/539* | (2006.01) |
| *B01J 20/26* | (2006.01) |
| *B01J 20/28* | (2006.01) |
| *B01J 20/32* | (2006.01) |

(52) U.S. Cl.
CPC .. *A61F 13/15699* (2013.01); *A61F 13/49001* (2013.01); *A61F 13/5323* (2013.01); *A61F 13/53713* (2013.01); *A61F 13/539* (2013.01); *B01J 20/26* (2013.01); *B01J 20/261* (2013.01); *B01J 20/28004* (2013.01); *B01J 20/28011* (2013.01); *B01J 20/28016* (2013.01); *B01J 20/28035* (2013.01); *B01J 20/3295* (2013.01); *A61F 2013/15414* (2013.01); *A61F 2013/53051* (2013.01); *A61F 2013/5395* (2013.01); *B01J 2220/68* (2013.01)

(58) Field of Classification Search
CPC .............. A61F 13/535; A61F 13/53713; A61F 2013/15414; A61F 2013/53051; A61F 2013/5395
See application file for complete search history.

(56) References Cited

U.S. PATENT DOCUMENTS

| | | | |
|---|---|---|---|
| 3,776,233 A | * | 12/1973 | Schaar .................. A61F 13/513 604/374 |
| 3,780,399 A | | 12/1973 | Morel |
| 3,814,100 A | | 6/1974 | Nystrand et al. |
| 4,055,180 A | | 10/1977 | Karami |
| 4,100,324 A | | 7/1978 | Anderson et al. |
| 4,100,922 A | * | 7/1978 | Hernandez ........ A61F 13/49001 604/389 |
| 4,360,021 A | | 11/1982 | Stima |
| 4,381,783 A | | 5/1983 | Elias |
| 4,434,010 A | | 2/1984 | Ash |
| 4,571,924 A | | 2/1986 | Bahrani |
| 4,646,362 A | | 3/1987 | Heran et al. |
| 4,670,011 A | | 6/1987 | Mesek |
| 4,673,402 A | | 6/1987 | Weisman et al. |
| 4,699,823 A | | 10/1987 | Kellenberger et al. |
| 4,715,918 A | | 12/1987 | Lang |
| 4,820,577 A | | 4/1989 | Morman et al. |
| 4,960,477 A | | 10/1990 | Mesek |
| 5,008,143 A | | 4/1991 | Armanini |
| 5,037,412 A | | 8/1991 | Tanzer et al. |
| 5,094,717 A | | 3/1992 | Manning et al. |
| 5,098,423 A | | 3/1992 | Pieniak et al. |

| | | | |
|---|---|---|---|
| 5,122,407 A | | 6/1992 | Yeo et al. |
| 5,149,335 A | | 9/1992 | Kellenberger et al. |
| 5,281,207 A | | 1/1994 | Chmielewski et al. |
| 5,294,478 A | | 3/1994 | Wanek et al. |
| 5,336,552 A | | 8/1994 | Strack et al. |
| 5,342,333 A | | 8/1994 | Tanzer et al. |
| 5,350,370 A | | 9/1994 | Jackson et al. |
| 5,356,403 A | | 10/1994 | Faulks et al. |
| 5,364,380 A | | 11/1994 | Tanzer et al. |
| 5,411,497 A | | 5/1995 | Tanzer et al. |
| 5,425,725 A | | 6/1995 | Tanzer et al. |
| 5,433,715 A | | 7/1995 | Tanzer et al. |
| 5,436,066 A | | 7/1995 | Chen |
| 5,458,592 A | | 10/1995 | Abuto et al. |
| 5,482,761 A | | 1/1996 | Palumbo et al. |
| 5,494,622 A | | 2/1996 | Heath et al. |
| 5,505,718 A | | 4/1996 | Roe et al. |
| 5,505,719 A | | 4/1996 | Cohen et al. |
| H1565 H | | 7/1996 | Brodof et al. |
| H1585 H | | 8/1996 | Ahr |
| 5,549,589 A | | 8/1996 | Horney et al. |
| 5,562,645 A | | 10/1996 | Tanzer et al. |
| 5,562,646 A | | 10/1996 | Goldman et al. |
| 5,567,744 A | | 10/1996 | Nagata et al. |
| 5,591,149 A | | 1/1997 | Cree et al. |
| 5,593,399 A | | 1/1997 | Tanzer et al. |
| 5,599,335 A | | 2/1997 | Goldman et al. |
| 5,601,542 A | | 2/1997 | Melius et al. |
| 5,650,222 A | | 7/1997 | DesMarais et al. |
| 5,653,702 A | | 8/1997 | Brohammer et al. |
| 5,669,894 A | | 9/1997 | Goldman et al. |
| 5,695,486 A | | 12/1997 | Broughton et al. |
| 5,714,027 A | | 2/1998 | Taub |
| 5,728,082 A | | 3/1998 | Gustafsson et al. |
| 5,741,241 A | | 4/1998 | Guidotti et al. |
| 5,749,259 A | | 5/1998 | Hamouda et al. |
| 5,763,331 A | | 6/1998 | Demhartner |
| 5,782,819 A | | 7/1998 | Tanzer et al. |
| 5,788,684 A | | 8/1998 | Abuto et al. |
| 5,800,418 A | | 9/1998 | Ahr |
| 5,800,419 A | | 9/1998 | Soga et al. |
| 5,810,796 A | | 9/1998 | Kimura et al. |
| 5,821,179 A | | 10/1998 | Masaki et al. |
| 5,853,403 A | | 12/1998 | Tanzer et al. |
| 5,863,288 A | | 1/1999 | Baker |
| 5,925,439 A | | 7/1999 | Haubach |
| 5,938,650 A | | 8/1999 | Baer et al. |
| 5,941,862 A | | 8/1999 | Haynes et al. |
| 5,944,706 A | | 8/1999 | Palumbo et al. |
| 5,947,947 A | | 9/1999 | Tanzer et al. |
| 5,994,614 A | | 11/1999 | Wada et al. |
| 6,024,822 A | | 2/2000 | Alper et al. |
| 6,046,377 A | | 4/2000 | Huntoon et al. |
| 6,068,620 A | | 5/2000 | Chmielewski |
| 6,071,549 A | | 6/2000 | Hansen |
| 6,086,950 A | | 7/2000 | Masaki et al. |
| 6,093,474 A | | 7/2000 | Sironi |
| 6,129,717 A | * | 10/2000 | Fujioka ............. A61F 13/15658 604/374 |
| 6,129,720 A | | 10/2000 | Blenke et al. |
| 6,140,550 A | | 10/2000 | Beihoffer et al. |
| 6,152,906 A | | 11/2000 | Faulks et al. |
| 6,162,959 A | | 12/2000 | O'Connor |
| 6,177,607 B1 | | 1/2001 | Blaney et al. |
| 6,238,379 B1 | | 5/2001 | Keuhn et al. |
| H1969 H | | 6/2001 | Fell et al. |
| 6,241,713 B1 | | 6/2001 | Gross et al. |
| 6,245,693 B1 | | 6/2001 | Gagliardi et al. |
| 6,258,076 B1 | | 7/2001 | Glaug et al. |
| 6,261,679 B1 | | 7/2001 | Chen et al. |
| H1978 H | | 8/2001 | Freiburger et al. |
| 6,290,686 B1 | | 9/2001 | Tanzer |
| 6,323,387 B1 | | 11/2001 | Soga et al. |
| 6,329,565 B1 | | 12/2001 | Dutkiewicz et al. |
| 6,368,990 B1 | | 4/2002 | Jennergren et al. |
| 6,383,960 B1 | | 5/2002 | Everett et al. |
| 6,392,116 B1 | | 5/2002 | Beihoffer et al. |
| 6,420,626 B1 | | 7/2002 | Erspamer et al. |
| 6,429,350 B1 | | 8/2002 | Tanzer et al. |

(56)                    References Cited

U.S. PATENT DOCUMENTS

| | | |
|---|---|---|
| 6,448,464 B1 | 9/2002 | Akin et al. |
| 6,458,877 B1 | 10/2002 | Ahmed et al. |
| 6,491,677 B1 | 12/2002 | Glaug et al. |
| 6,500,251 B1 | 12/2002 | Andes et al. |
| 6,534,572 B1 | 3/2003 | Ahmed et al. |
| 6,548,732 B2 | 4/2003 | Erdman et al. |
| 6,569,137 B2 | 5/2003 | Suzuki et al. |
| 6,570,056 B1 | 5/2003 | Tanzer et al. |
| 6,575,952 B2 | 6/2003 | Kirk et al. |
| 6,592,960 B1 | 7/2003 | Suzuki et al. |
| 6,610,900 B1 | 8/2003 | Tanzer |
| 6,632,209 B1 * | 10/2003 | Chmielewski .... A61F 13/49406 |
| | | 604/385.01 |
| 6,645,407 B2 | 11/2003 | Kellenberger et al. |
| 6,677,498 B2 | 1/2004 | Chen et al. |
| 6,680,423 B1 | 1/2004 | Tanzer |
| 6,689,205 B1 | 2/2004 | Brückner et al. |
| 6,689,934 B2 | 2/2004 | Dodge et al. |
| 6,700,035 B2 | 3/2004 | Yoshimasa |
| 6,702,800 B1 | 3/2004 | Vukos et al. |
| 6,730,069 B2 | 5/2004 | Tanzer et al. |
| 6,790,798 B1 | 9/2004 | Suzuki et al. |
| 6,797,360 B2 | 9/2004 | Varona |
| 6,849,672 B2 | 2/2005 | Mehawej et al. |
| 6,875,264 B2 | 4/2005 | Zimmermann et al. |
| 6,878,433 B2 | 4/2005 | Curro et al. |
| 6,899,776 B2 | 5/2005 | Bahlmann et al. |
| 6,965,058 B1 | 11/2005 | Raidel et al. |
| 6,972,011 B2 | 12/2005 | Maeda et al. |
| 7,321,007 B2 | 1/2008 | Gagliardi et al. |
| 7,699,825 B2 | 4/2010 | Nakagawa et al. |
| 7,722,590 B2 | 5/2010 | Tsuji et al. |
| 7,744,576 B2 | 6/2010 | Busam et al. |
| 7,750,203 B2 | 7/2010 | Becker et al. |
| 7,759,540 B2 | 7/2010 | Litvay et al. |
| 7,767,878 B2 | 8/2010 | Suzuki |
| 7,838,721 B2 | 11/2010 | Chen |
| 7,838,722 B2 | 11/2010 | Blessing et al. |
| 7,847,145 B2 | 12/2010 | Kurita et al. |
| 7,872,168 B2 | 1/2011 | Sawyer et al. |
| 7,994,233 B2 | 8/2011 | Mehawej et al. |
| 7,994,384 B2 | 8/2011 | Qin et al. |
| 8,148,598 B2 | 4/2012 | Tsang et al. |
| 8,163,124 B2 | 4/2012 | Moriura et al. |
| 8,180,603 B2 | 5/2012 | Blessing et al. |
| 8,187,240 B2 | 5/2012 | Busam et al. |
| 8,211,076 B2 | 7/2012 | Sugiyama et al. |
| 8,735,646 B2 | 5/2014 | Beruda et al. |
| 8,802,918 B2 | 8/2014 | Fukudome et al. |
| 8,901,367 B2 | 12/2014 | Sanz et al. |
| 8,979,815 B2 | 3/2015 | Roe et al. |
| 9,066,835 B2 | 6/2015 | Okawa et al. |
| 9,072,634 B2 | 7/2015 | Hundorf et al. |
| 9,216,118 B2 | 12/2015 | Roe et al. |
| 9,233,519 B2 | 1/2016 | Yamaguchi et al. |
| 9,295,593 B2 | 3/2016 | Malderen |
| 9,468,566 B2 | 10/2016 | Rosati et al. |
| 9,486,371 B2 | 11/2016 | Wirtz et al. |
| 9,549,858 B2 | 1/2017 | Yang |
| 9,707,135 B2 | 7/2017 | Sheldon et al. |
| 9,713,557 B2 | 7/2017 | Arizti et al. |
| 10,071,002 B2 | 9/2018 | Bianchi et al. |
| 10,123,916 B2 | 11/2018 | Weisman et al. |
| 10,201,462 B2 * | 2/2019 | Wright .............. B01J 20/28035 |
| 10,307,298 B2 | 6/2019 | Varona et al. |
| 10,675,195 B2 | 6/2020 | Greco et al. |
| 10,772,769 B2 | 9/2020 | Maele |
| 11,090,203 B2 * | 8/2021 | Wright .............. A61F 13/49001 |
| 2002/0115969 A1 | 8/2002 | Maeda et al. |
| 2003/0119394 A1 | 6/2003 | Ranganathan et al. |
| 2003/0119402 A1 | 6/2003 | Melius et al. |
| 2003/0120231 A1 | 6/2003 | Wang et al. |
| 2003/0129915 A1 | 7/2003 | Harriz |
| 2003/0144379 A1 * | 7/2003 | Mitchell ................. A61L 15/60 |
| | | 252/194 |

| | | |
|---|---|---|
| 2003/0149414 A1 | 8/2003 | Mehawej |
| 2003/0175418 A1 | 9/2003 | Muthiah et al. |
| 2004/0015142 A1 | 1/2004 | Johnston et al. |
| 2004/0054342 A1 | 3/2004 | Newbill et al. |
| 2004/0111848 A1 | 6/2004 | Miyamoto et al. |
| 2004/0116014 A1 | 6/2004 | Soerens et al. |
| 2004/0162536 A1 | 8/2004 | Becker et al. |
| 2004/0167486 A1 | 8/2004 | Busam et al. |
| 2004/0204697 A1 | 10/2004 | Litvay |
| 2004/0211361 A1 | 10/2004 | Suzuki et al. |
| 2005/0165371 A1 | 7/2005 | Giacometti |
| 2005/0166799 A1 | 8/2005 | Fuller et al. |
| 2005/0171499 A1 | 8/2005 | Nigam et al. |
| 2005/0215962 A1 | 9/2005 | Litvay et al. |
| 2006/0004334 A1 | 1/2006 | Schlinz et al. |
| 2006/0021695 A1 | 2/2006 | Blessing et al. |
| 2006/0069367 A1 | 3/2006 | Waksmundzki et al. |
| 2006/0167424 A1 | 7/2006 | Chang et al. |
| 2006/0206074 A1 * | 9/2006 | Bernal .................. A61F 13/536 |
| | | 604/385.101 |
| 2007/0093164 A1 | 4/2007 | Nakaoka |
| 2007/0156107 A1 | 7/2007 | Kimura et al. |
| 2008/0103466 A1 | 5/2008 | Ehmsperger et al. |
| 2008/0172017 A1 * | 7/2008 | Carlucci ........... A61F 13/15203 |
| | | 604/374 |
| 2009/0076473 A1 | 3/2009 | Kasai et al. |
| 2009/0087636 A1 | 4/2009 | Yasuda et al. |
| 2009/0112175 A1 | 4/2009 | Bissah et al. |
| 2010/0036342 A1 | 2/2010 | Carlucci et al. |
| 2010/0057032 A1 | 3/2010 | Hardegree |
| 2010/0063470 A1 | 3/2010 | Suzuki et al. |
| 2010/0100065 A1 | 4/2010 | Bianco et al. |
| 2010/0323885 A1 | 12/2010 | Herfert et al. |
| 2011/0046597 A1 | 2/2011 | Mizutani et al. |
| 2011/0111199 A1 | 5/2011 | Takatori et al. |
| 2011/0151228 A1 | 6/2011 | Takatori et al. |
| 2011/0276019 A1 | 11/2011 | Kakimoto et al. |
| 2012/0029456 A1 | 2/2012 | Takatori et al. |
| 2012/0071852 A1 | 3/2012 | Tsang et al. |
| 2012/0089108 A1 | 4/2012 | Jeda et al. |
| 2012/0175056 A1 | 7/2012 | Tsang et al. |
| 2012/0203191 A1 | 8/2012 | Maruo et al. |
| 2012/0238977 A1 | 9/2012 | Oku et al. |
| 2012/0288701 A1 | 11/2012 | Matsushita et al. |
| 2012/0308799 A1 | 12/2012 | Yamaguchi et al. |
| 2012/0328861 A1 | 12/2012 | Hinayama et al. |
| 2012/0328862 A1 | 12/2012 | Fukudome et al. |
| 2013/0018349 A1 | 1/2013 | Takatori et al. |
| 2013/0046263 A1 | 2/2013 | Fukudome et al. |
| 2013/0072890 A1 | 3/2013 | Yang |
| 2013/0116644 A1 | 5/2013 | Wei et al. |
| 2013/0178814 A1 | 7/2013 | Matsushita et al. |
| 2014/0005623 A1 | 1/2014 | Wirtz et al. |
| 2014/0180230 A1 | 6/2014 | Tsang et al. |
| 2014/0276508 A1 | 9/2014 | Wright et al. |
| 2014/0276518 A1 | 9/2014 | Varona et al. |
| 2014/0296817 A1 | 10/2014 | Malderen |
| 2014/0303582 A1 | 10/2014 | Wright et al. |
| 2015/0005727 A1 | 1/2015 | Matsushita et al. |
| 2015/0038929 A1 | 2/2015 | Malderen |
| 2016/0151213 A1 | 6/2016 | Bauduin et al. |
| 2018/0064583 A1 | 3/2018 | Maele |

FOREIGN PATENT DOCUMENTS

| | | | |
|---|---|---|---|
| CN | 1310741 A | 8/2001 | |
| CN | 1612801 A | 5/2005 | |
| CN | 1655697 A | 8/2005 | |
| CN | 1985783 A | 6/2007 | |
| CN | 101426461 A | 5/2009 | |
| CN | 101641067 A | 2/2010 | |
| CN | 102325511 A | 1/2012 | |
| CN | 202288650 U | 7/2012 | |
| CN | 103002847 A | 3/2013 | |
| EP | 0212618 A1 | 3/1987 | |
| EP | 0540041 A1 | 5/1993 | |
| EP | 0829245 A2 | 3/1998 | |
| EP | 0725616 B1 | 3/1999 | |
| EP | 0947549 A1 | 10/1999 | |

(56) References Cited

FOREIGN PATENT DOCUMENTS

| | | | |
|---|---|---|---|
| EP | 1428581 | A1 | 6/2004 |
| EP | 1447066 | A1 | 8/2004 |
| EP | 1447067 | A1 | 8/2004 |
| EP | 1561442 | A1 | 8/2005 |
| EP | 1609448 | A1 | 12/2005 |
| EP | 1627618 | A1 | 2/2006 |
| EP | 1800638 | A1 | 6/2007 |
| EP | 2111835 | A1 | 10/2009 |
| EP | 2550946 | A1 | 1/2013 |
| EP | 2586409 | A1 | 5/2013 |
| EP | 2986263 | B1 | 1/2017 |
| EP | 2086487 | B1 | 9/2018 |
| GB | 2252047 | A | 7/1992 |
| JP | H06190001 | A | 7/1994 |
| JP | H07132126 | A | 5/1995 |
| JP | H08246395 | A | 9/1996 |
| JP | H10118115 | A | 5/1998 |
| JP | H11506964 | A | 6/1999 |
| JP | 2000238161 | A | 9/2000 |
| JP | 2002159533 | A | 6/2002 |
| JP | 2002345883 | A | 12/2002 |
| JP | 2004358797 | A | 12/2004 |
| JP | 2006305327 | A | 11/2006 |
| JP | 2007061171 | A | 3/2007 |
| JP | 2007167193 | A | 7/2007 |
| JP | 2007222646 | A | 9/2007 |
| JP | 2008132056 | A | 6/2008 |
| JP | 2009061230 | A | 3/2009 |
| JP | 2010520948 | A | 6/2010 |
| JP | 2010522595 | A | 7/2010 |
| JP | 3172565 | U | 12/2011 |
| JP | 2011530335 | A | 12/2011 |
| JP | 2013010361 | A | 1/2013 |
| KR | 100336053 | B1 | 11/2002 |
| TL | 2007098492 | A2 | 8/2007 |
| WO | 9503019 | A1 | 2/1995 |
| WO | 9511654 | A1 | 5/1995 |
| WO | 9521596 | A1 | 8/1995 |
| WO | 9705841 | A1 | 2/1997 |
| WO | 0041663 | A1 | 7/2000 |
| WO | 02053363 | A2 | 7/2002 |
| WO | 03059228 | A2 | 7/2003 |
| WO | 2004098473 | A1 | 11/2004 |
| WO | 2006007185 | A1 | 1/2006 |
| WO | 2008117109 | A1 | 10/2008 |
| WO | 2011063975 | A1 | 6/2011 |
| WO | 2011128790 | A2 | 10/2011 |
| WO | 2012009297 | A1 | 1/2012 |
| WO | 2012/052172 | * | 4/2012 ............ A61F 13/15 |
| WO | 2013099634 | A1 | 7/2013 |
| WO | 2014145312 | A2 | 9/2014 |
| WO | 2015002934 | A2 | 1/2015 |

OTHER PUBLICATIONS

2nd Office Action from Canadian Application No. 2,643,482, dated Jun. 20, 2014; 2 pages.

2nd Office Action from Chinese Application No. 200780014162.9 filed Feb. 22, 2007, dated Aug. 29, 20127pages.

3rd Office Action from Chinese Application No. 200780014162.9 filed Feb. 22, 2007, dated Feb. 27, 20138 pages.

4th Office Action from Chinese Application No. 200780014162.9, dated Aug. 9, 2013; 14 pages.

Decision on Rejection from Chinese Application No. 200780014162.9, dated Dec. 4, 2013; 16 pages.

International Preliminary Report on Patentability issued and published Aug. 26, 2008during the prosecution of International Application No. PCT/US2007/062614.

International Search Report dated Aug. 27, 2014, during the prosecution of International Application No. PCT/US2014/030066.

International Search Report dated Dec. 17, 2007, and published Feb. 21, 2008, during the prosecution of International Application No. PCT/US2007/062614.

International Search Report dated Jan. 12, 2015, during the prosecution of International Application No. PCT/US2014/045027.

International Search Report dated Jul. 30, 2014, during the prosecution of International Application No. PCT/US2014/026148.

International Search Report dated Oct. 28, 2014, during the prosecution of International Application No. PCT/US2014/030051.

Notification of Transmittal of International Preliminary Report on Patentability dated Jun. 5, 2015, during the prosecution of International Application No. PCT/US2014/45027; 26 pages.

Notification of Transmittal of International Preliminary Report on Patentability dated Nov. 24, 2015, during the prosecution of International Application No. PCT/US2014/030051; 48 pages.

Office Action from Chinese Application No. 200780014162.9 filed Feb. 22, 2007, dated Feb. 29, 20129 pages.

Partial Supplementary EP Search Report, issued in EP Application No. 14763071.9 dated Sep. 232016 [9 pages].

Partial Supplementary EP Search Report, issued in EP Application No. 14819386.5 dated Feb. 8, 2017 [7 pages].

Supplementary (partial) EP Search Report, issued in EP Application No. 14819386.5 dated May 11, 2017 [14 pages].

Written Opinion dated Aug. 27, 2014, during the prosecution of International Application No. PCT/US2014/030066.

Written Opinion dated Dec. 17, 2007, and published Aug. 22, 2008 during the prosecution of International Application No. PCT/US2007/062614.

Written Opinion dated Jan. 12, 2015, during the prosecution of International Application No. PCT/US2014/045027.

Written Opinion dated Jul. 30, 2014, during the prosecution of International Application No. PCT/US2014/026148.

Written Opinion dated Oct. 28, 2014, during the prosecution of International Application No. PCT/US2014/030051.

Written Opinion of the International Preliminary Examining Authority issued Jun. 5, 2015during the prosecution of International Application No. PCT/US2014/030051; 32 pages.

* cited by examiner

240''

(a)

(b)

(c)

610b

610c

610a

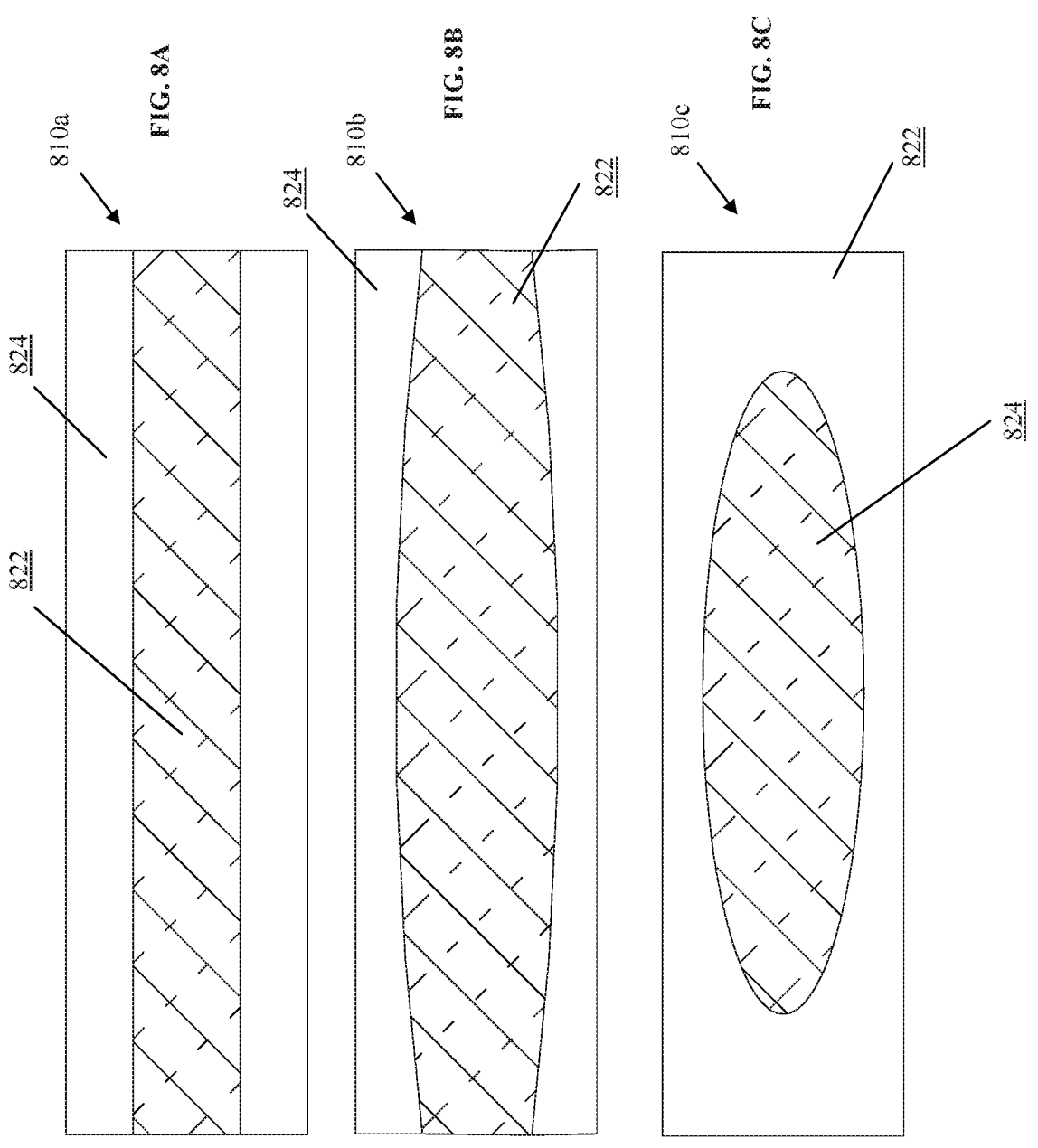

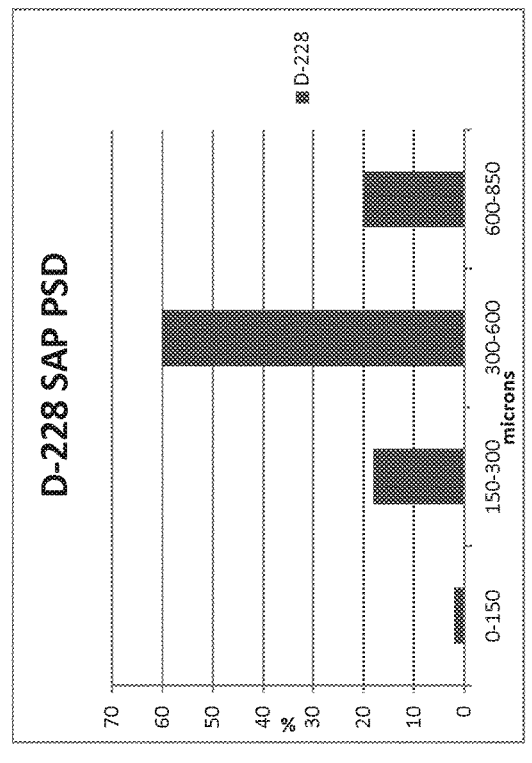
FIG. 10B
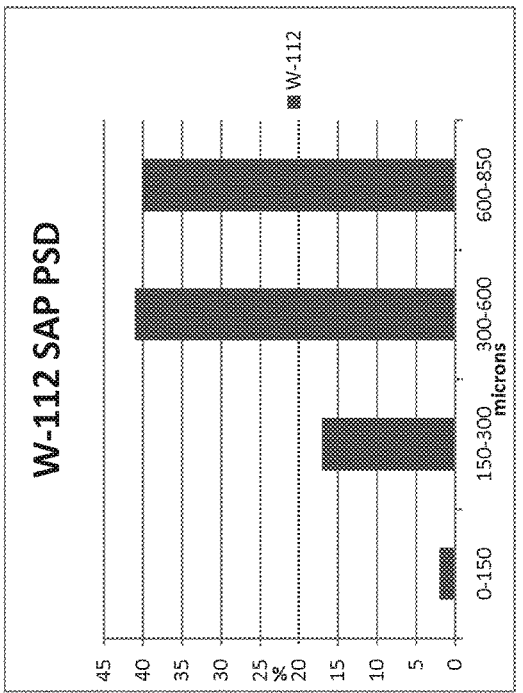
FIG. 10A
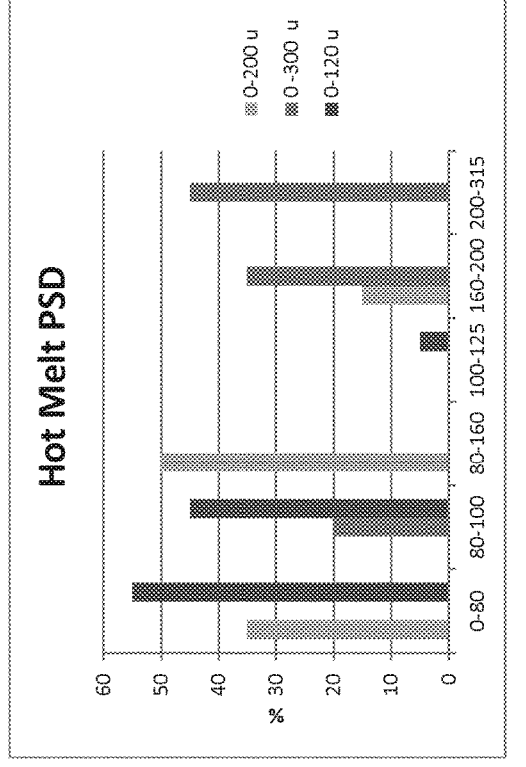
FIG. 10C

ABSORBENT COMPOSITE, AN ABSORBENT ARTICLE EMPLOYING THE SAME, AND METHODS, SYSTEMS, AND APPARATUS FOR MAKING THE ABSORBENT COMPOSITE AND/OR ARTICLE

The present application is a Continuation application of U.S. application Ser. No. 16/206,764, filed Nov. 30, 2018 (now U.S. Pat. No. 11,090,203), which is a Continuation application of U.S. application Ser. No. 14/321,773 filed on Jul. 1, 2014 (now U.S. Pat. No. 10,201,462), which claims the benefit of U.S. Provisional Application Ser. No. 61/842,961 filed on Jul. 3, 2013 and U.S. Provisional Application No. 61/843,986 filed on Jul. 9, 2013. Each of these disclosures is hereby incorporated by reference for all purposes and made a part of the present disclosure.

The present disclosure relates generally to an absorbent core composite and disposable absorbent garment incorporating the core composite. The disclosure also relates to a system, apparatus, and a method of making the absorbent composite or the disposable absorbent article. Such disposable absorbent articles include diapers, training pants, adult incontinence products, bodily exudates absorbing products, feminine hygiene products, and other absorbent products (collectively "disposable absorbent articles").

Prior disposable absorbent articles typically employ three basic structural elements: a topsheet that forms the inner surface, a backsheet that forms the outer surface, and an absorbent core that is interposed between the topsheet and the backsheet. The topsheet is designed to allow liquid to pass from outside the absorbent article through the topsheet and into the absorbent core. The topsheet may be made out of a range of liquid and vapor permeable hydrophilic or hydrophobic materials.

The backsheet is designed to prevent fluid from passing from the absorbent core through the backsheet and out of the absorbent article. The backsheet may be made out of an impermeable film that extends the full width of the article or a combination of cloth-like material and impermeable film. The backsheet may also have vapor transmission properties ("breathability") that allow vapor to pass through the backsheet without releasing fluid stored in the absorbent core. The backsheet may also be made from a liquid impermeable but vapor transmittable non-woven material such as spunbond, melt-blow, spun-bond ("SMS"); spun-bond, melt-blown, melt-blown, spun-bond ("SMMS"); micro, nano, or splitable fibers; spun melt or spun laced; carded; and the like.

The absorbent core is designed to contain and distribute fluid that passes through the topsheet. A typical absorbent core is made out of a high or super absorbent polymer (SAP) stabilized by an absorbent matrix. SAP is commonly made out of materials such as polyvinyl alcohol, polyacrylates, various grafted starches, and cross-linked sodium polyacrylate. SAP can be in the form of particles, fibers, foams, web, spheres, agglomerates of regular or irregular shapes, and film. The absorbent matrix is typically a de-fiberized wood pulp or similar material. The absorbent matrix is very bulky relative to the topsheet, backsheet, and SAP. Most of a diaper's thickness comes from the absorbent core.

Increasingly, consumers of absorbent articles are demanding thinner absorbent articles. To meet these demands, manufactures are decreasing the thickness of absorbent articles by decreasing the amount of absorbent matrix used in absorbent cores. Although the resulting absorbent cores are thinner, they suffer in performance. As the amount of absorbent matrix is reduced, it is less effective in stabilizing the SAP—preventing the SAP from migrating within the absorbent core. As SAP migrates within the core, the absorbent core loses its effectiveness and no longer has uniform absorbency. For example, SAP that is not contained tends to bunch up in wetted areas and is inefficient for handling subsequent discharges.

Manufacturers have attempted to solve this problem by creating small, individual SAP pockets or by gluing the SAP. These solutions, however, have been largely unsuccessful. The SAP pockets merely limit the migration to movement within the pockets. However, because there is still a movement of the particles, the absorbent core does not exhibit uniform absorbency. Gluing the SAP stabilizes the SAP, but results in an uncomfortably stiff absorbent core and a loss in the SAP's swelling capacity.

Securing the SAP by adhesive, cover layer, or other manner can also affect the performance of the SAP during product use. In some instances, SAP and product performance are sacrificed for core stability and ease of manufacture. Because the absorbent core is pressed against the user's skin during article use, the wearer is very sensitive to the touch and feel of the core. Thus, the introduction of even a minor physical feature in an absorbent core design can have a great impact on the comfort of the user.

There is a continuing need for an improved absorbent product featuring reduced composite thickness, but maintaining or improving fluid handling properties and sure fit and comfort. The specifications of U.S. Pat. No. 8,148,598 and International Application PCT/US2014/030051 (the '051 Application), each of which is commonly assigned and designates at least one common inventor as the present application, describes a prior improvement to the state of the art and serves as background to the present disclosure. The disclosures both documents are hereby incorporated by reference, in its entirety, for all purposes and made a part of the present disclosure. The present disclosure may, in one respect, be regarded as continuing and furthering the effort to provide improved absorbent products and systems, apparatus, and methods of manufacturing.

BRIEF SUMMARY

The present disclosure relates generally to an absorbent core composite and disposable absorbent garment incorporating the absorbent composite. The disclosure also relates to a system, apparatus, and a method of making the absorbent composite or the disposable absorbent article. In one aspect, improved absorbent core composites are provided with advantageous swell capacities or void volumes. In another aspect, absorbent core composites (and methods and systems of making same) are provided with void volume increase mechanisms, configurations, or structures. Such functionalities are preferably triggered or activated during use, prior use, or during manufacture. In yet another aspect, absorbent core composites are provided with improved liquid receipt, retention, and distribution functionalities, as well as manufacturability.

In one aspect, an absorbent core composite is disclosed for incorporation into a disposable absorbent article. The absorbent core composite include a first material layer (preferably nonwoven) and a second material layer (preferably nonwoven) at least partially secured (e.g., by bond sites, bond points, adhesive, and the like) to the first material layer to define at least one pocket therebetween. Preferably, multiple pockets are defined, except in the case of where a generally uniform layer or bed of absorbent is preferred or better suited for the application. The pocket is said have a fixed initial volume (e.g., as defined by its physical configuration). Further, an aggregate of absorbent particles is provided in the pocket(s) to occupy a portion of the fixed initial volume. The absorbent particles are preferably SAP particles and is characterized by a dry volume associated with a dry state and a swell volume associated with a liquid saturation state. In respect to or for the pocket, the aggregate is characterized by a collective dry volume and a collective swell volume, wherein the pocket has an initial configuration that retains the aggregate therein.

In another aspect, an absorbent core composite is disclosed for incorporation into a disposable absorbent article. The absorbent core composite has a first material layer, a second material layer at least partially secured to the first material layer to define a plurality of pockets, each of the pockets having a fixed initial volume, and absorbent particles provided in aggregates each disposed in one of the pockets. The absorbent particles are characterized by a dry volume associated with a dry state and swell volume associated with a liquid saturation state, and wherein, for each pocket, the aggregate is characterized by a collective dry volume and a collective swell volume, the collective swell volume being greater than the initial pocket volume. Each pocket is expandable from an initial configuration partially defining the initial volume toward an expanded configuration under which an increased pocket volume accommodates the collective swell volume. For each pocket, the first material layer has a pressure sensitive configuration, such that pressure generated by the aggregate transforming into the collective swell volume initiates expansion of the first material layer from an initial configuration partially defining the initial volume toward an expanded configuration under which an increased pocket volume accommodates the collective swell volume.

In another aspect, a disposable absorbent article (e.g., a diaper, training pants, adult incontinence articles, and the like) is disclosed having a chassis body defined by a first end margin and a second end margin longitudinally spaced from the first end margin. The end margins partially define front and back waist regions that are positioned about a waist of a user during wear of the absorbent article. The article further includes a topsheet, a backsheet, and an absorbent core composite disposed between the topsheet and backsheet. The composite includes a first nonwoven layer, a second nonwoven layer at least partially secured to the first nonwoven layer to define a plurality of pockets therebetween, the pockets having a fixed initial volume, and an aggregate of SAP particles disposed in the pocket to occupy a portion of the fixed initial volume. The SAP particles are characterized by a dry volume associated with a dry state and a swell volume associated with a liquid saturation state, and wherein, for the pocket, the aggregate is characterized by a collective dry volume and a collective swell volume, wherein the pocket has an initial configuration that retains the aggregate. Further, an outside surface of the first nonwoven layer exhibits surface discontinuities in the initial configuration of the pocket. The outside surface is extendible, however, to substantially remove the discontinuities and place the pocket in an expanded configuration defining an increased pocket volume. The discontinuities may be corrugations, folds, pleats, and other (temporary) deformations that are removable upon extension of the outside surface.

In another absorbent core composite for incorporation into a disposable absorbent article, the absorbent core composite has a first material layer having an outside surface forming a bodyside outer surface of the absorbent core composite, a second material layer having an outside surface forming an opposite outer surface of said absorbent core composite, a first layer of absorbent particles disposed between the outer surfaces of the absorbent composite and having an average size dimension (i.e., the average width or diameter of the particles), and a second layer of absorbent particles disposed between the outer surfaces of the absorbent composite and having an average size dimension less than the average size dimension of the first layer. The first layer of particles are situated substantially in the first material layer and the second layer of particles are situated substantially in the second material layer. In a further embodiment, an intermediate layer is disposed between the first and second material layers and contains another layer of absorbent particles. The densities of the two or three layers may be selected to achieve a desired gradient of absorbent particles (and absorbent properties).

In another aspect, a method is disclosed for forming an absorbent composite for incorporation into a disposable absorbent article. The method entails providing a first material layer, positioning a second material layer beneath the second material layer, providing a supply of absorbent particles composed of a population of a first absorbent particles having a first average size dimension and a second population of absorbent particles having a second average size dimension less than the first average size dimension, and depositing the first and second populations of absorbent particles onto the first material layer such that absorbent particles of the first population are maintained in the first material layer and absorbent particles of the second population filter through the first material layer and settle in the second material layer. The first material layer may be a low density nonwoven having a density between 0.01 to 0.03 g/cc and the second material layer may be of a higher density nonwoven.

In another aspect, another absorbent core composite is disclosed for incorporation into a disposable absorbent article. The absorbent core composite includes a bodyside first material layer (nonwoven), and a second material layer (nonwoven), wherein the first and second material layers define a space therebetween. The defined space contains a layer of superabsorbent particles, which includes a population of SAP particles and a population of non-SAP spacing particles that are smaller than the SAP particles and generally positioned between two or more SAP particles, thereby spacing two or more SAP particles from one another. Further, the spacing particles may be selected from the group of spacing particles consisting of: inert particles; water-soluble particles; volatile particles; ion-exchange particles; and combinations thereof.

In another aspect, another disposable absorbent article is disclosed having a chassis body defined by a first end margin and a second end margin longitudinally spaced from the first end margin, the end margins partially defining front and back waist regions that are positioned about a waist of a user during wear of the absorbent article. The article further includes a topsheet, a backsheet, and an absorbent composite disposed between the topsheet and backsheet. The absorbent composite includes a first material layer having an outside surface, a second material layer having an outside surface, a first layer of absorbent particles provided between the outside surfaces, and a second layer of absorbent particles provided between the outside surfaces, wherein the second layer of absorbent particles has absorbent properties different from said first layer.

A method is also disclosed for making an absorbent composite for incorporation into a disposable absorbent garment. The method entails conveying a first sheet of a first nonwoven layer, depositing absorbent particles on the first sheet, and applying a second sheet of a second nonwoven layer over the deposited absorbent particles and first sheet, thereby forming a composite including two material layers sandwiching absorbent particles therebetween. The method also provides bonding the first and second material layers to secure, at least partially, absorbent particles therebetween. In one embodiment, prior to conveying the first sheet, a surface of the first sheet is deformed to form laterally elongatable surface discontinuities.

The disclosure also provides for systems and methods for making the articles and composites discussed above or in the Detail Description, or illustrated in the Figures. It should also be noted that various embodiments are disclosed herein. Some embodiments feature elements (design features, steps or components) that are not described as being specifically incorporated into other embodiments. Many more variations or embodiments are contemplated, however, and such further combinations or incorporation of elements will be evident to one skilled in the art in possession of the present disclosure.

Lastly, the absorbent composite features means for altering the initial pocket configuration during use (e.g., in the event if liquid intake by the absorbent article) to accommodate the swell volume of the aggregate. For example, the altering means may be provided by the pocket being expandable from the initial configuration defining the initial volume toward an expanded configuration under which an increased pocket volume accommodates the collective swell volume, the collective swell volume being greater than the collective dry volume. Further, such means for altering the initial pocket configuration means at least one of the first and second material layers being elongatable in response to swelling of SAP aggregate in said pocket. The subject elongatable material layer may be corrugated or may have a plurality of folds therein extending in the longitudinal direction. The altering means may also be provided by a breakable substrate such as tissue, dry-crepe tissue or a slitted substrate (weakened material). The altering means may, in the alternative, be provided by breakable bonds, such as breakable bond point or water-soluble adhesive, that otherwise secure the material layers to define the pocket(s) and contain the SAP aggregate (i.e., during SAP swell).

BRIEF DESCRIPTION OF THE DRAWINGS

FIG. 3A is an elevated cross-sectional view of a section of an absorbent composite having an elongatable substrate partially defining a pocket SAP aggregate, according to the

Figures 3A, 3B, 3C, 3D, 3E:
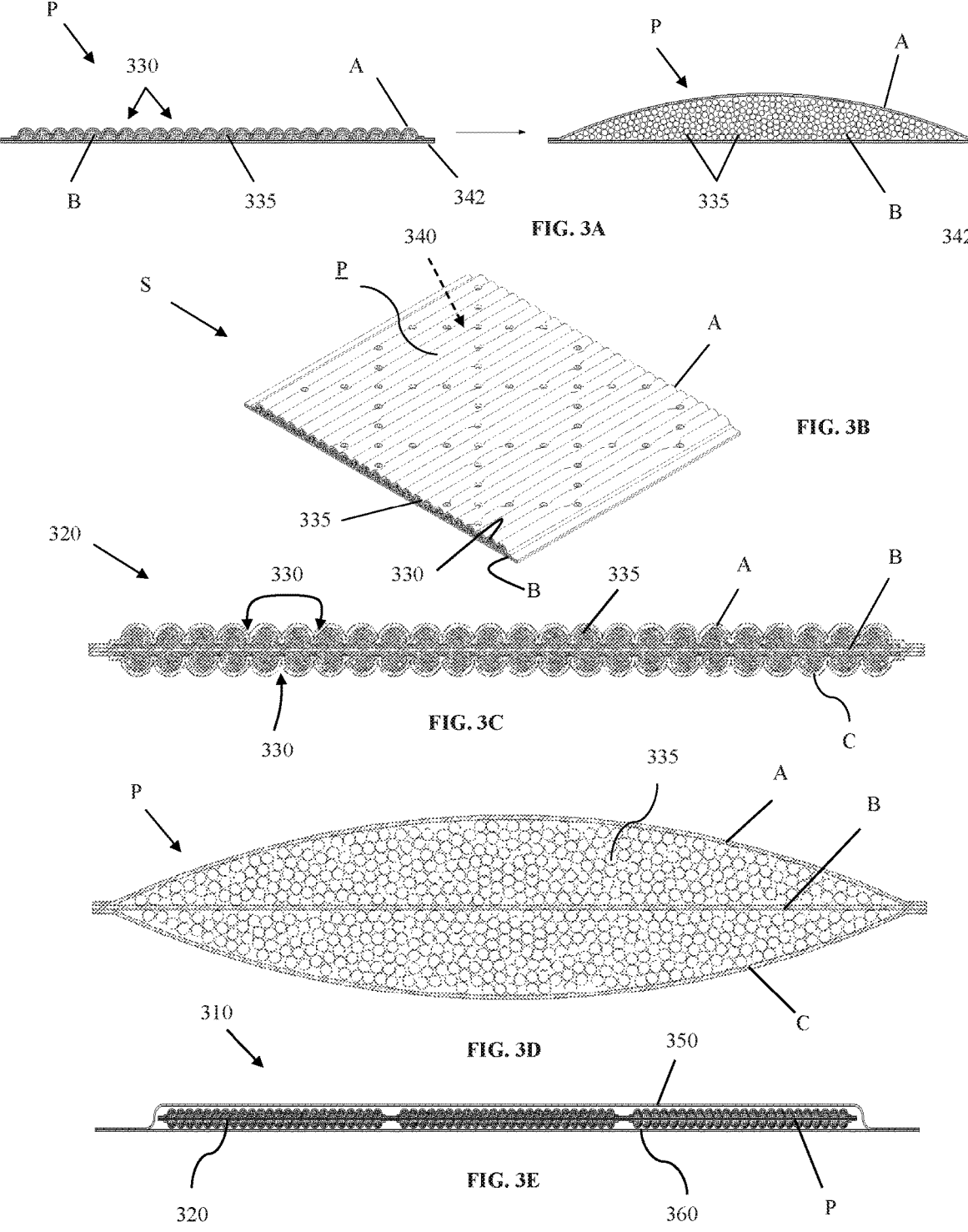
Figures 4, 5A, 5B:
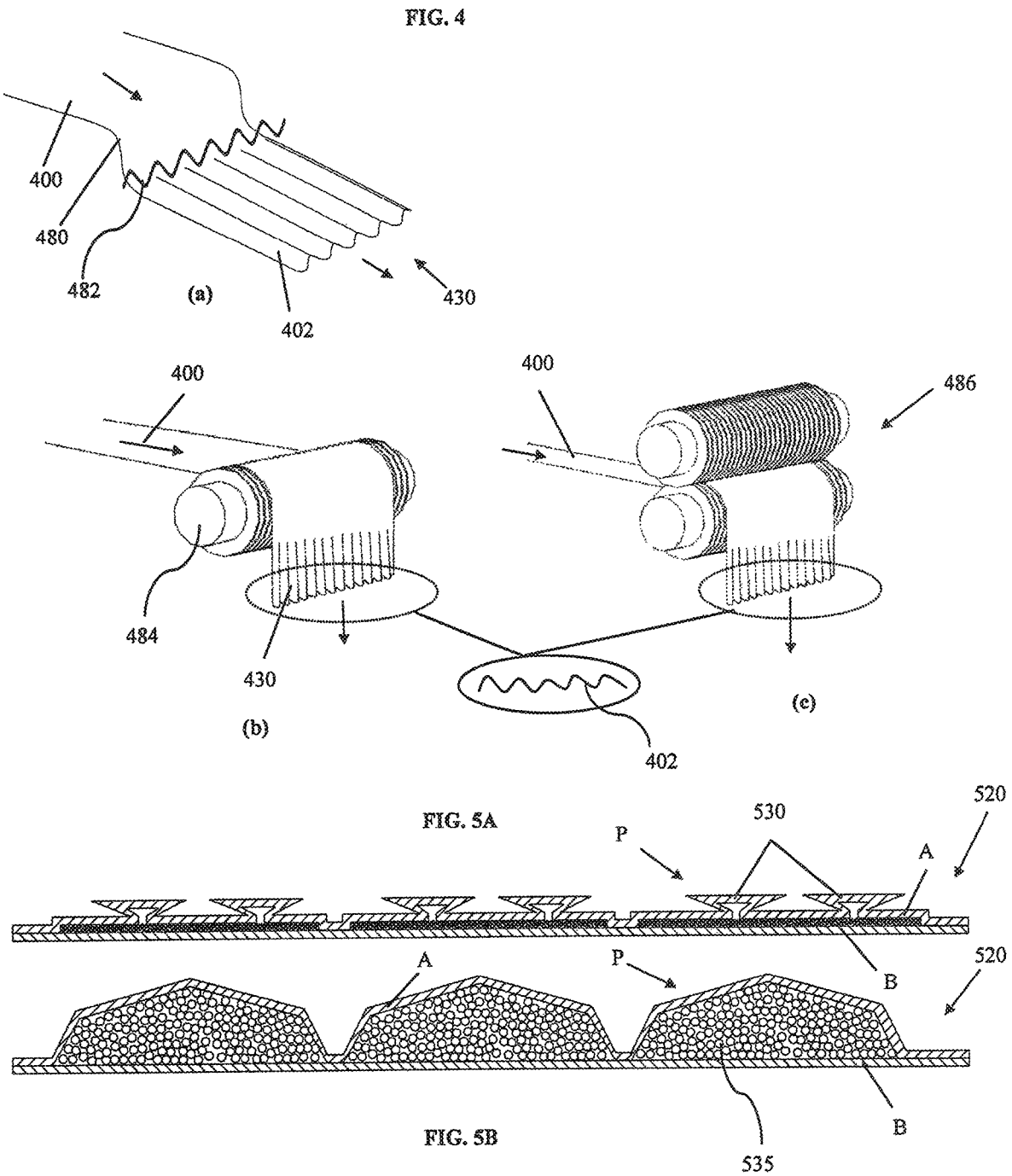
Figures 6A, 6B, 6C:
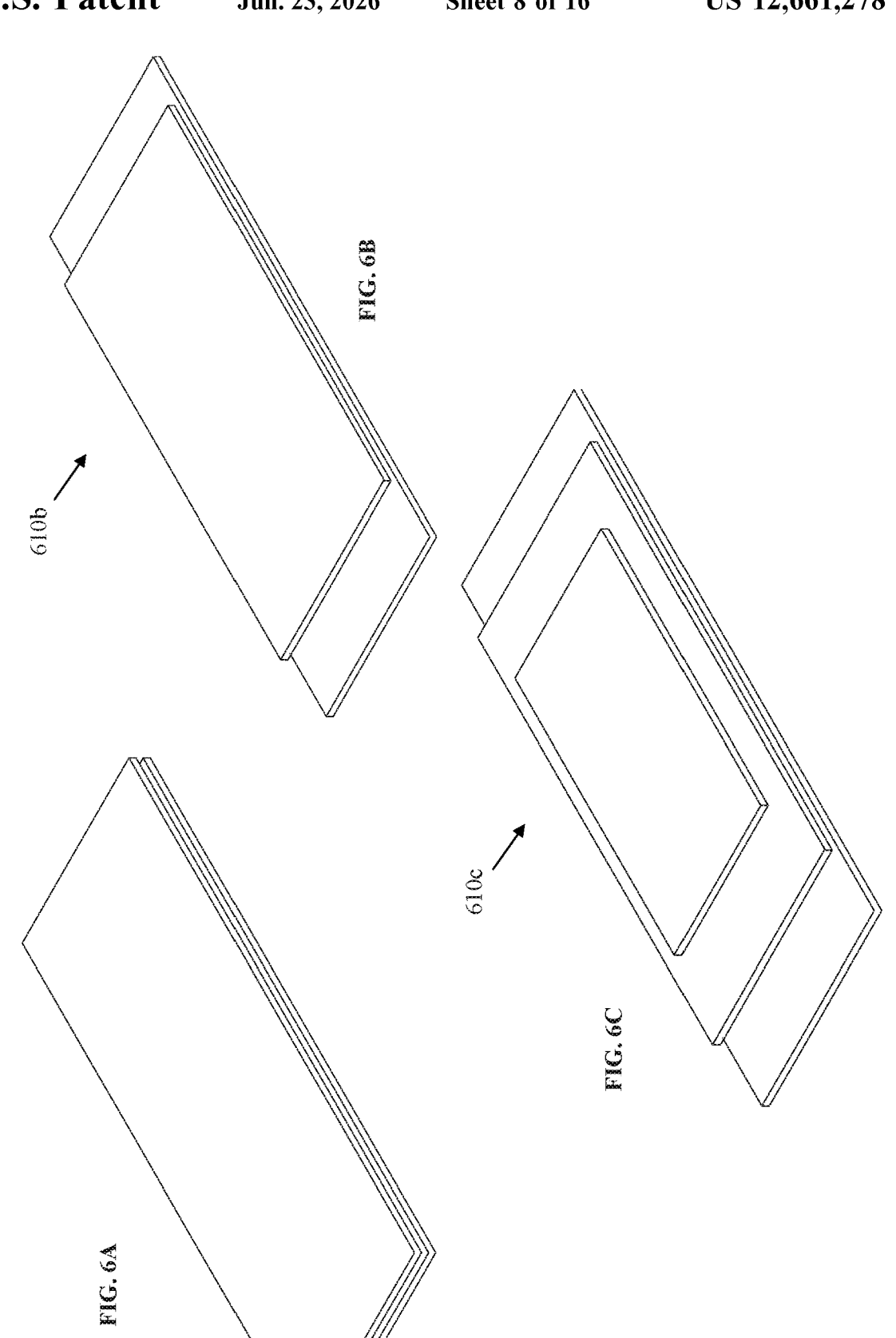
Figures 7A, 7B:
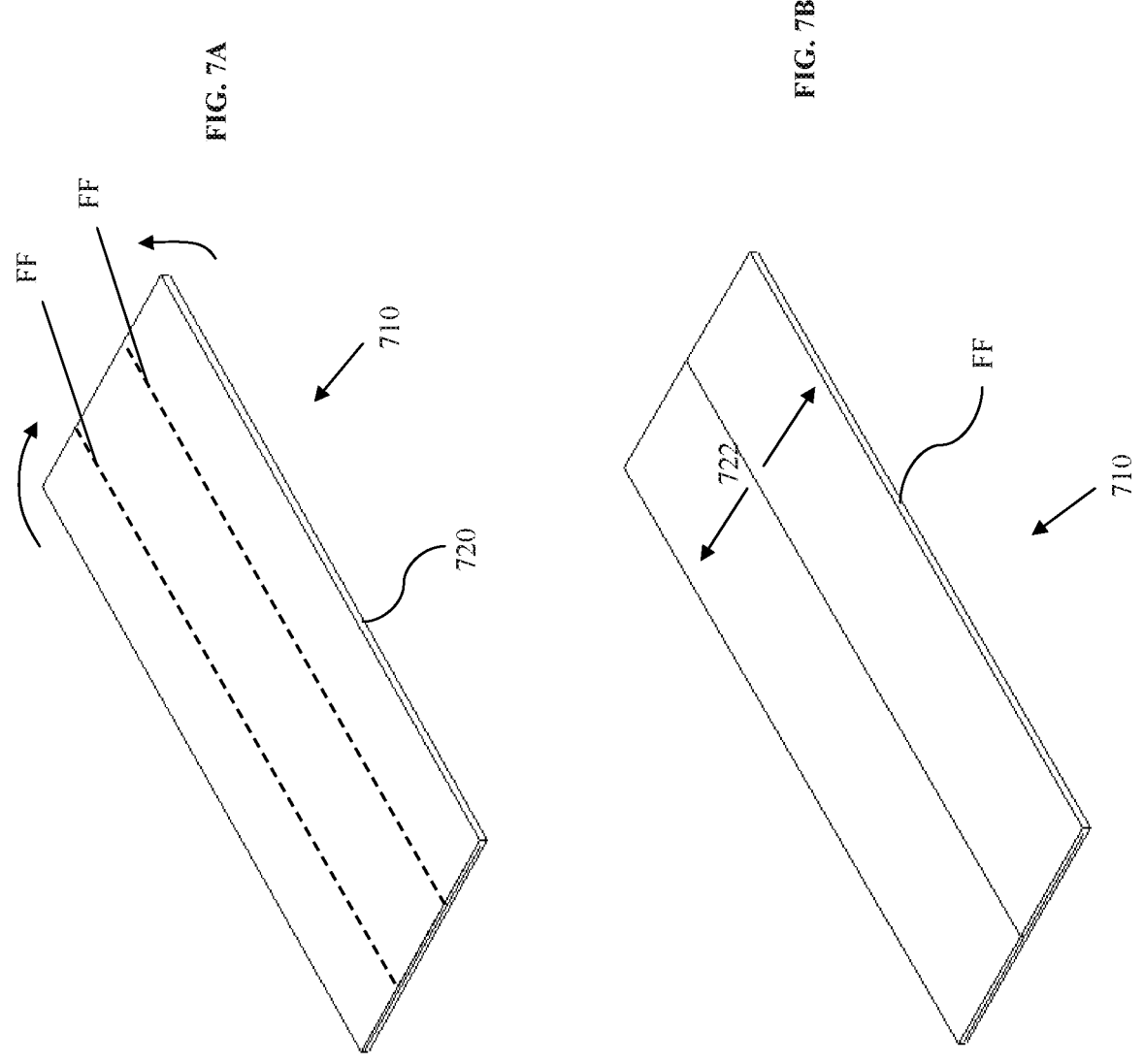
Figures 9A, 9B, 9C, 9D:
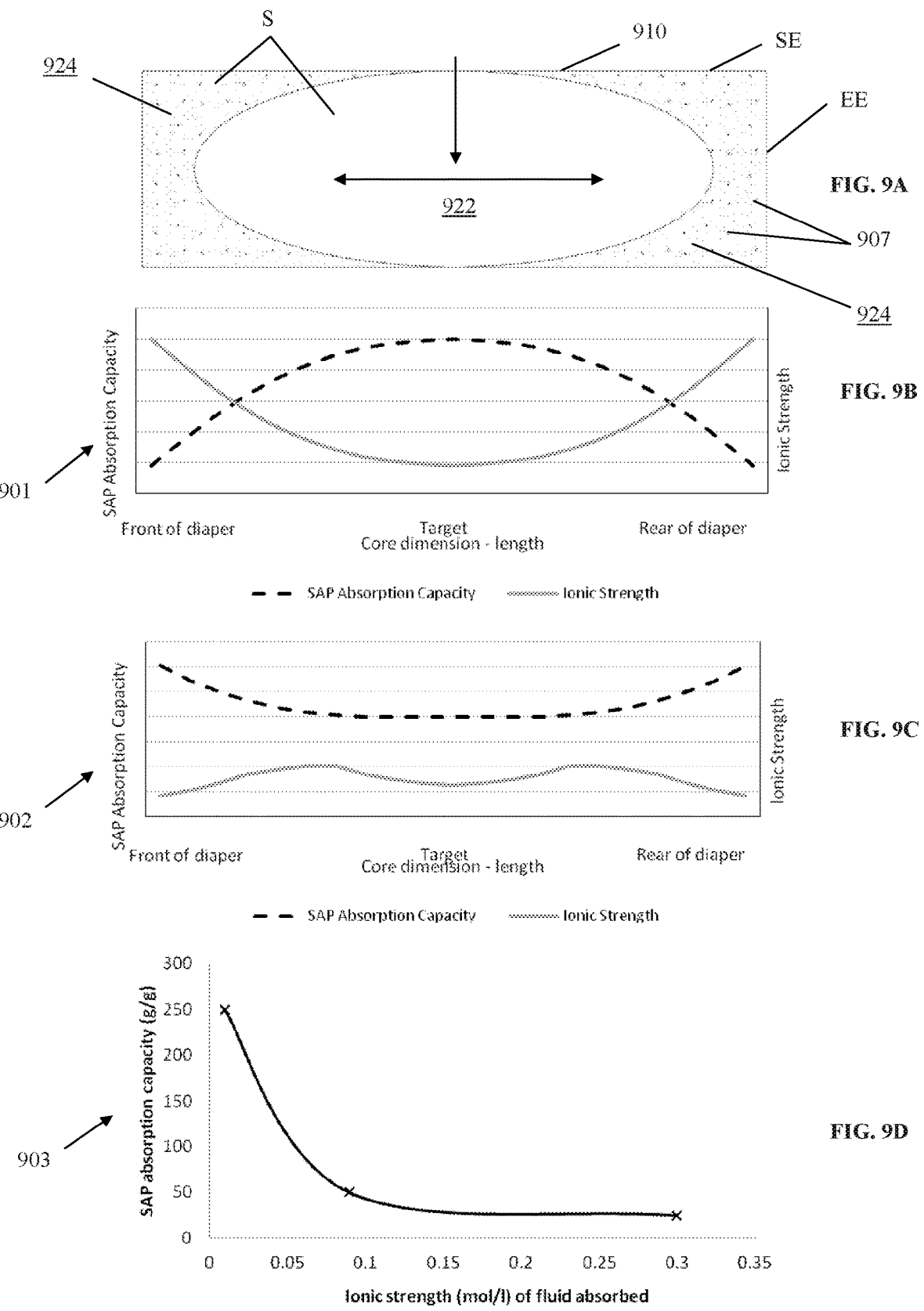
Figures 11, 12:
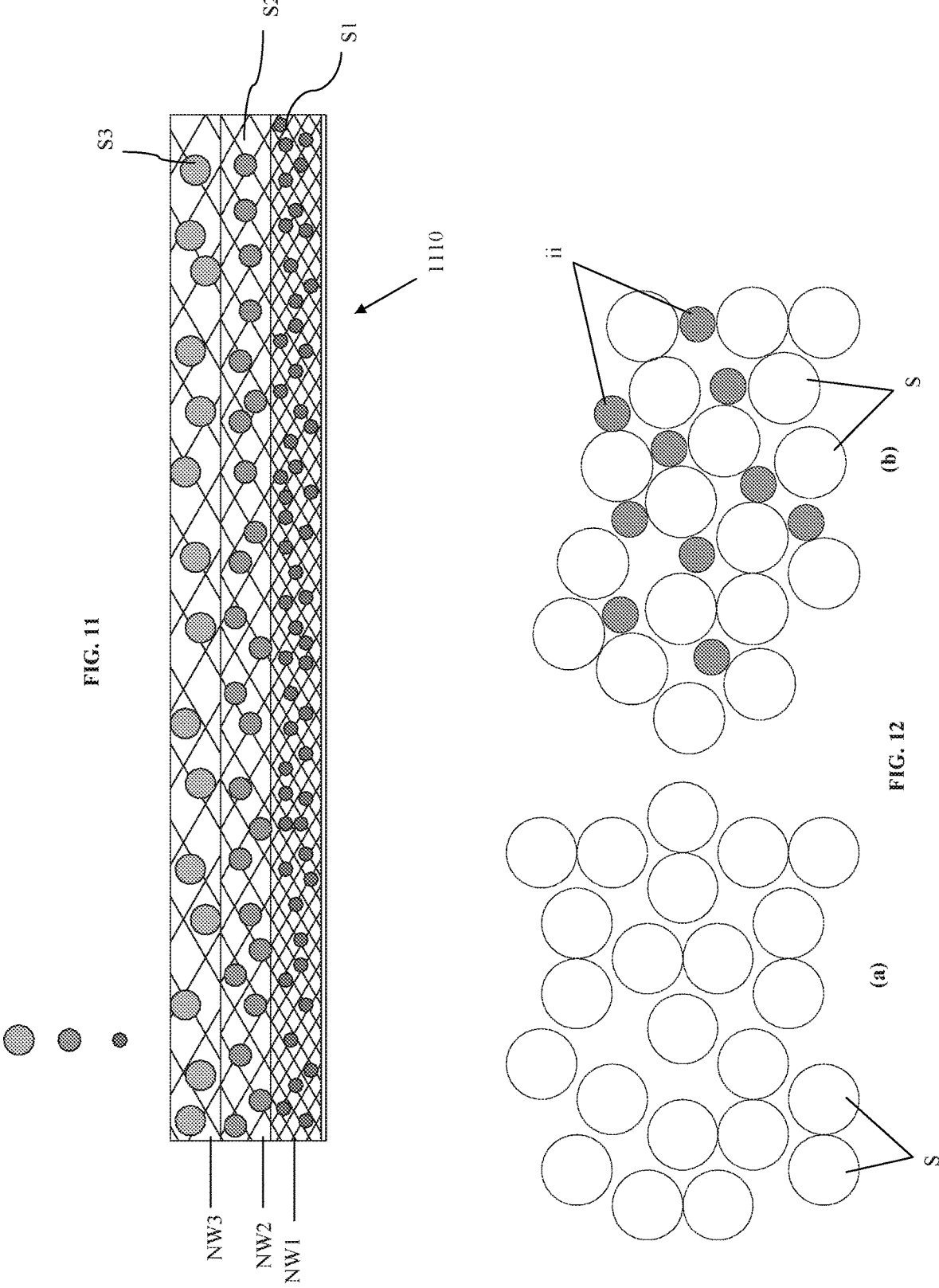
Figure 13:
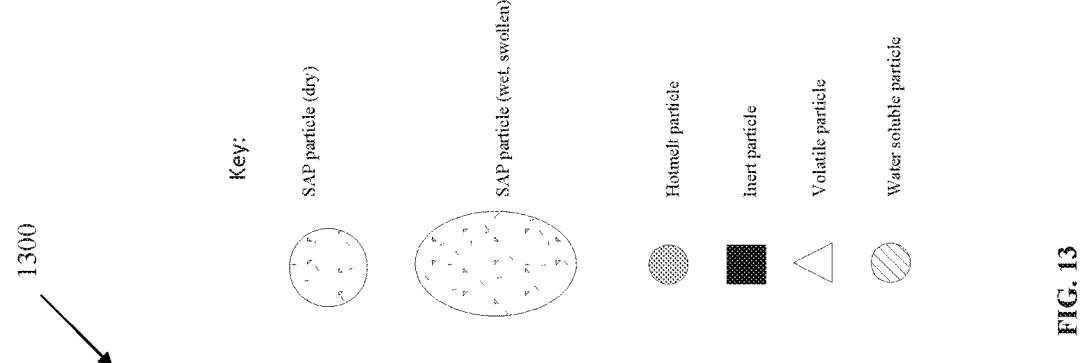
Figures 14, 15:
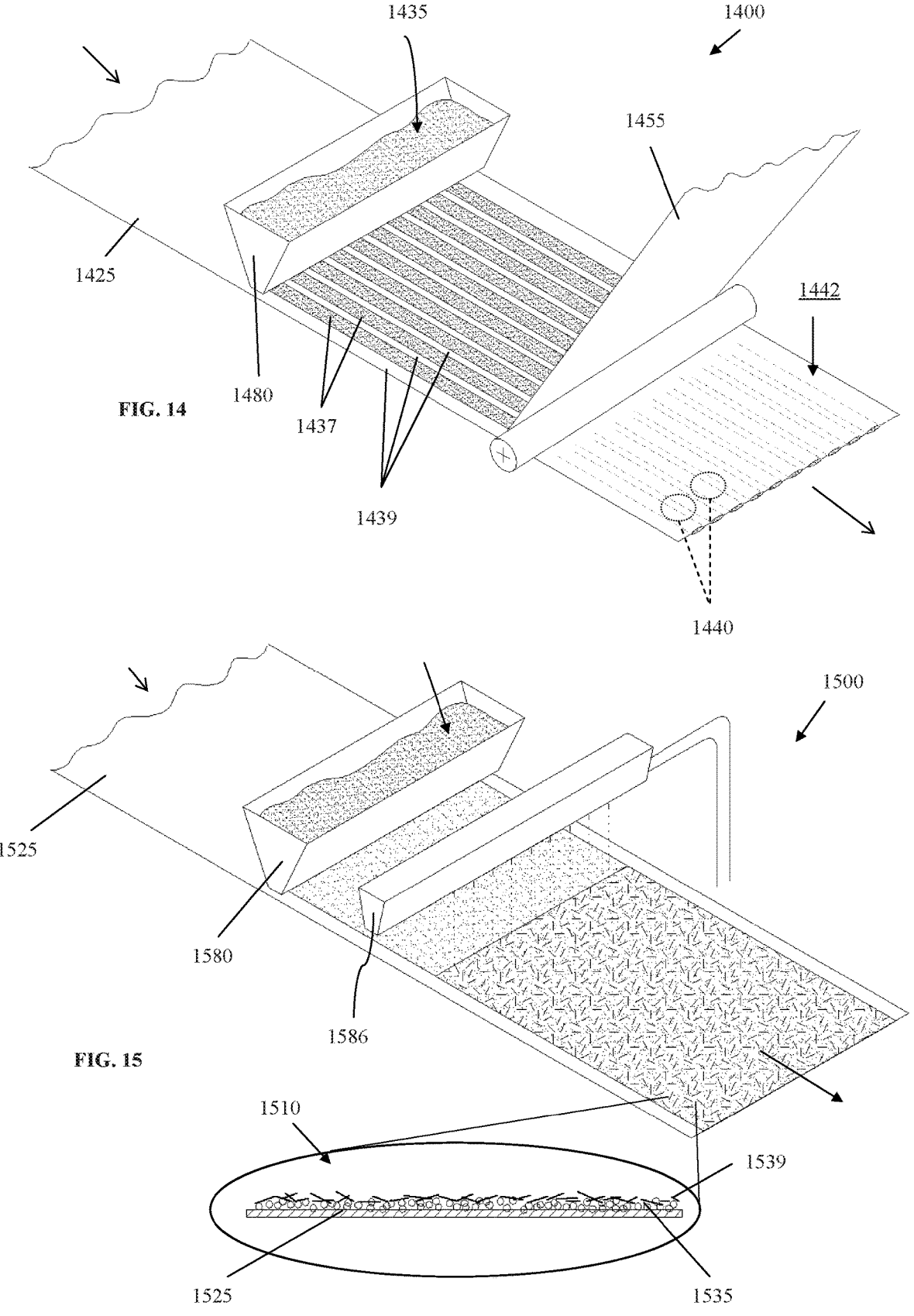
Figures 16, 17:
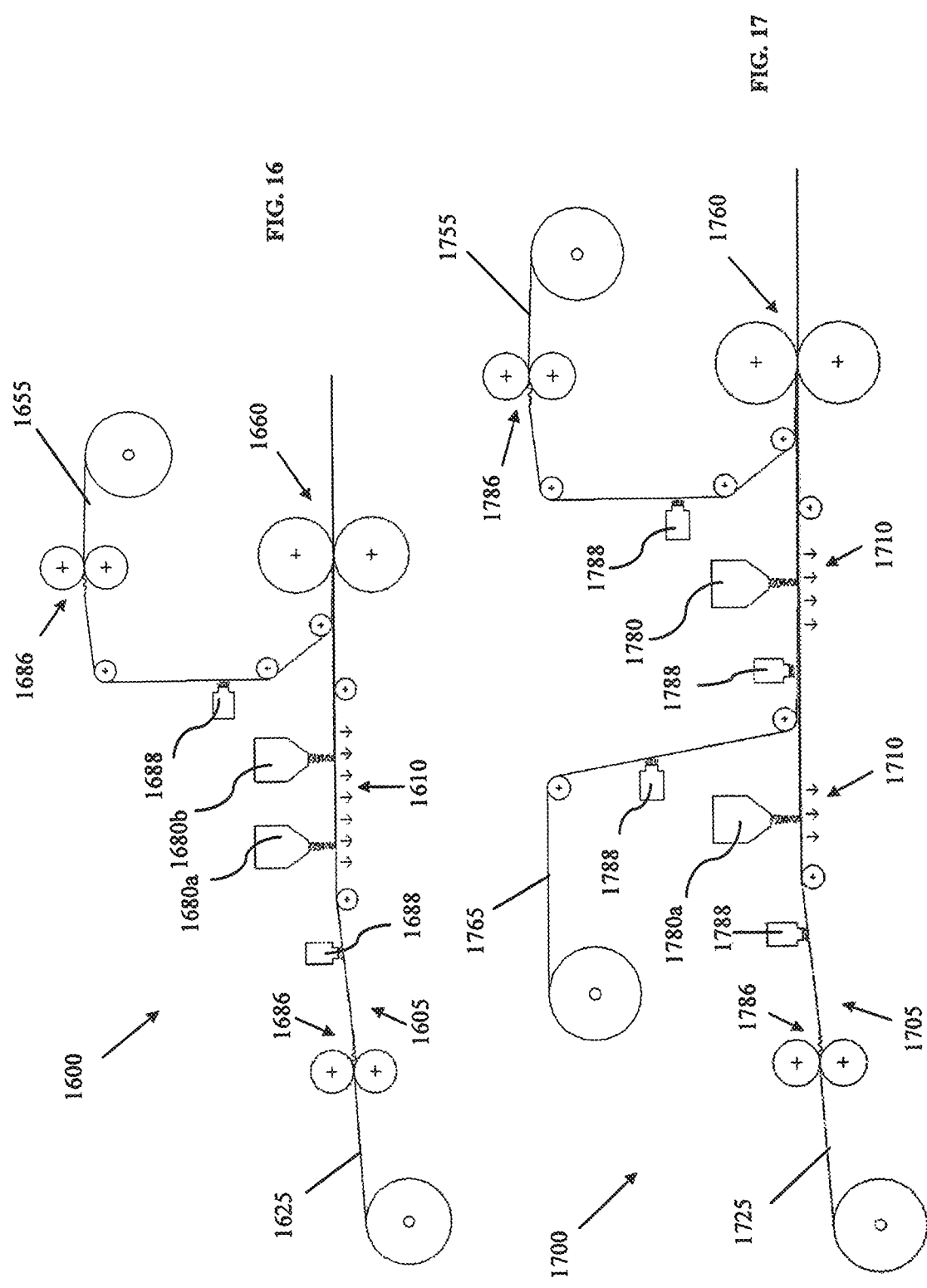

6 present disclosure, the pocket shown first in a pre-activated and in a fixed initial configuration and then, activated an in an expanded configuration;

FIG. 3B is a perspective view of a sheet of the absorbent composite in FIG. 3A;

FIG. 3C is an elevated cross-sectional view of a section of an alternative absorbent core composite having an elongatable substrate, according to the present disclosure, shown in a pre-activated state;

FIG. 3D is an elevated cross-sectional view of the section of an alternative absorbent core composite in FIG. 3C, shown in an activated or expanded state;

FIG. 3E is an elevated cross-sectional view of a section of a diaper incorporating the absorbent composite in FIG. 3C;

FIG. 4 are simplified illustrations of portions of a process of riffling or corrugating a non-woven sheet for incorporation into a absorbent composite, and equipment suitable for use in the process;

FIG. 5A is a simplified illustration of an absorbent core composite having an elongatable substrate according to the present disclosure;

FIG. 5B is a simplified illustration of the absorbent core composite of FIG. 5A in an activated state;

FIGS. 6A-6C are simplified illustrations of multi-layer absorbent core composites, according to the present disclosure;

FIGS. 7A-7B are simplified illustrations of folded absorbent core composites according to the present disclosure;

FIGS. 8A-8C are simplified illustrations in plan view of absorbent core composites featuring cross-directional profiling of absorbent properties, according to the present disclosure;

FIGS. 9A-9C are simplified diagrams illustrating the relation between travel of liquid on an absorbent core and changes in absorbent property of the SAP in areas along said liquid travel;

FIG. 9D is graph showing the relation between SAP absorbent capacity and target liquid ionic strength;

FIG. 10A-10B is a depiction of a bar chart displaying suitable SAP particle size distribution;

FIG. 10C is a depiction of a bar chart displaying suitable hotmelt particle size distribution;

FIG. 11 is a simplified illustration of an absorbent composite exhibiting layered particle size filtration on nonwoven layer;

FIG. 12 is a simplified illustration of a SAP aggregate with and without inert particle spacers;

FIG. 13 is graphical chart of simplified illustrations of SAP aggregate constitutions during bonding and product use;

FIG. 14 is a simplified illustration of a system and process for making an absorbent composite sheet having lanes of SAP, according to one embodiment;

FIG. 15 is a simplified illustration of a system and process of making an absorbent composite sheet utilizing hotmelt fibers in the composite according to one embodiment;

FIG. 16 is schematic illustrating a system and process for making an absorbent composite according to various embodiment; and FIG. 17 is a schematic illustrating a system and process for making an absorbent composite according to various embodiments.

DETAILED DESCRIPTION

Figure 1A:
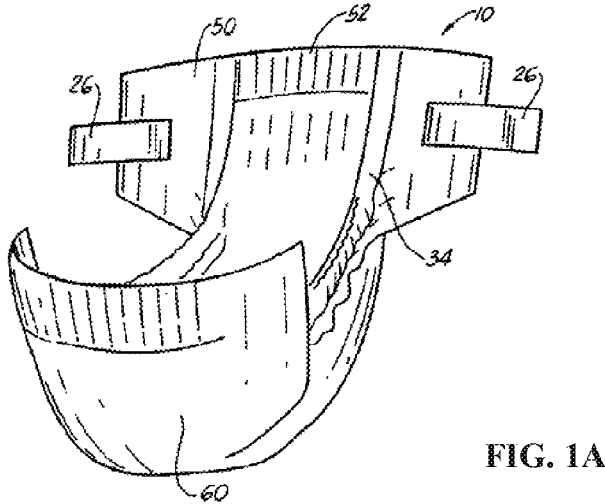
FIG. 1A is a perspective view of a disposable absorbent article incorporating an absorbent composite according to the present disclosure.

Referring first to FIG. 1A, a disposable absorbent article is shown in the form of a diaper 10. The diaper 10 is a type of absorbent article that readily incorporates, as its central functional component, an absorbent core composite according to the present disclosure. The basic components of the diaper 10 are a topsheet 50, a backsheet 60, and an absorbent core 46 (not shown in FIG. 1A but in FIGS. 1B and 1C) disposed between the backsheet 60 and topsheet 50. The diaper 10 also features upstanding barrier cuffs 34 that extend longitudinally along the diaper and are elasticized to conform to the buttocks of the wearer. Additionally, the diaper includes an elastic waist band 52 and fastening elements 26. Element 26, is extendible to and engages the corresponding opposing end of the diaper 10 to secure the diaper 10 about the wearer.

Figure 1B:
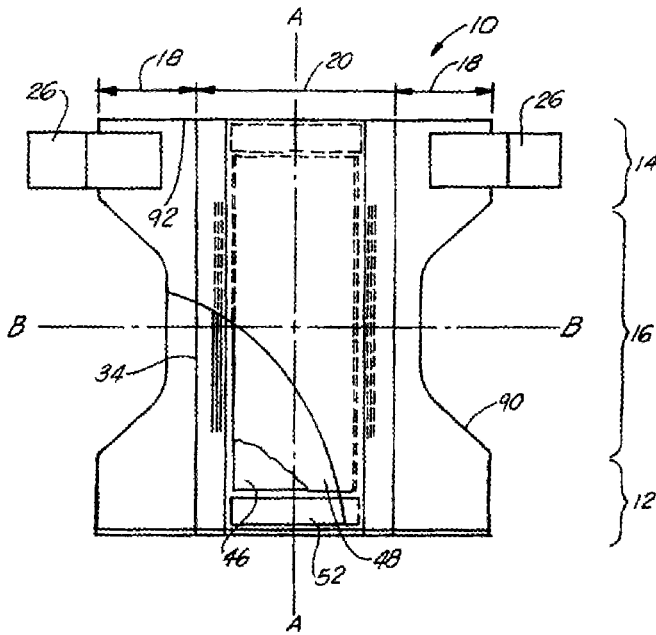
FIG. 1B is a top plan view of the disposable absorbent article in FIG. 1A, in a flat and extended position.

FIG. 1B illustrates a composite web structure of the diaper 10 in a generally flat and unfolded configuration. As will be explained below, the web structure may be subsequently trimmed, folded, sealed, welded and/or otherwise manipulated to form a disposable diaper 10 in a finished or final form. To facilitate description of the diaper 10, the description refers to a longitudinally extending axis AA, a laterally extending central axis BB, a pair of longitudinally extending side edges 90, and a pair of end edges 92 that extend between side edges 90. The imaginary lines AA and BB shown are also referred to as the diaper's longitudinal and lateral centerlines, respectively. Generally, when discussing the positions or orientations of various elements of the diaper 10, references made to lateral and longitudinal directions or extensions relate or correspond with the axes AA and BB (unless referring specifically to the context of that particular element). It should also be noted that the direction of the longitudinal centerline AA generally corresponds with the machine direction (MD) of the diaper 10 while the direction of the lateral centerline BB corresponds with the cross machine direction (CD) of the diaper. The machine direction (MD) of a diaper element such as a topsheet or backsheet, and other nonwovens which contain fibrous elements, can be determined by observing the alignment and/or condition of the fibers in the diaper element. The fibers normally align with the machine direction. This can be observed, for example, under a microscope long after the diaper has been manufactured.

Along the longitudinal axis AA, the diaper 10 includes a first end region or front waist region 12, a second end region or back waist region 14, and a crotch region 16 disposed therebetween. Each of the front and back waist regions 12, 14 is characterized by a pair of ear regions or ears 18, which are located on either side of a central body portion 20 and extend laterally from the side edges 90. A fastening structure 26 (e.g., a conventional tape fastener) is affixed to each of the ears 18 along the back waist region 14 of diaper 10. When the diaper 10 is worn about the waist, the front waist region 12 is fitted adjacent the front waist area of the wearer, the back waist region 14 is fitted adjacent the back waist area, and the crotch region 16 fits about and underneath the crotch area. To properly secure the diaper 10 to the wearer, the ears 18 of the back waist region 14 are brought around the waist of the wearer and toward the front and into alignment with the ears 18 of the front waist region 12.

Figure 1C:
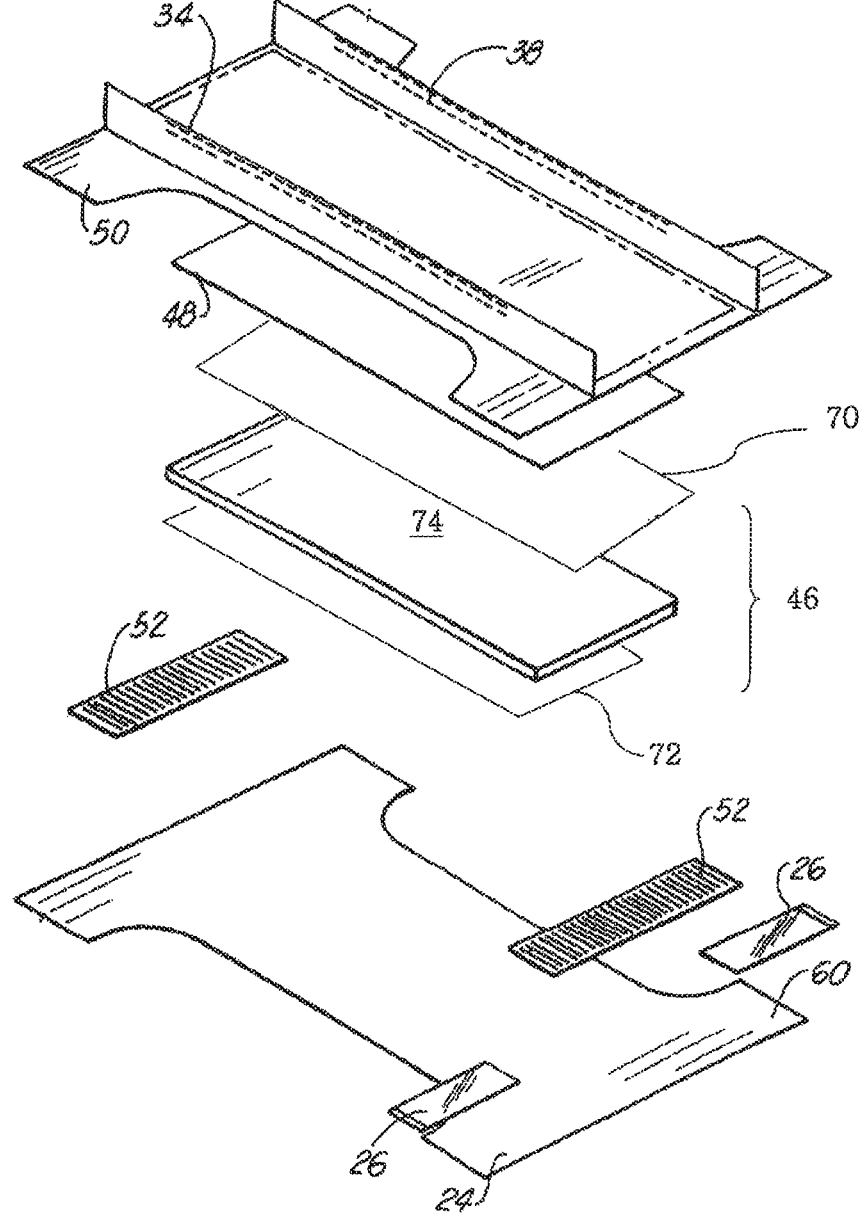
FIG. 1C is an exploded view of the disposable absorbent article in FIG. 1A.

FIG. 1B reveals an absorbent core 46 disposed beneath the topsheet 48 and an acquisition and distribution layer (ADL) 48. FIG. 1C is an exploded view of the diaper of FIGS. 1A and 1B, and illustrates, in simplified form, the absorbent core 46 as a multi-component laminate having a generally rectangular shape. In other preferred embodiments, the absorbent core 46 takes on an hourglass shape featuring a laterally narrowed central region. The absorbent core 46 is generally composed of a top nonwoven layer 70, a bottom nonwoven layer 72, and a layer, body, or collection of absorbent materials 74 therebetween. Prior to incorporation into the diaper, the absorbent core body 46 is often referred to as an absorbent composite or absorbent core composite. A generally planar extension of the absorbent composite may be presented and referred to as a web or an absorbent composite sheet during manufacturing and as a product or article of manufacture. The present disclosure is primarily directed to an improved absorbent composite construction and systems and methods of making the composite or an absorbent composite sheet from which absorbent composite is sourced. The present disclosure is also directed to a disposable absorbent article in which the absorbent composite is incorporated as the absorbent core.

An absorbent core composite of the type addressed by certain embodiments of the present disclosure features pockets or containers in which SAP is retained. Other improved absorbent core composites are described which also exhibit improved fluid handling performance and are amendable to thin-core constructions, but may not necessarily feature or require pockets. Without pockets, these composites can be made with a generally uniform profile and depth.

Figure 1D:
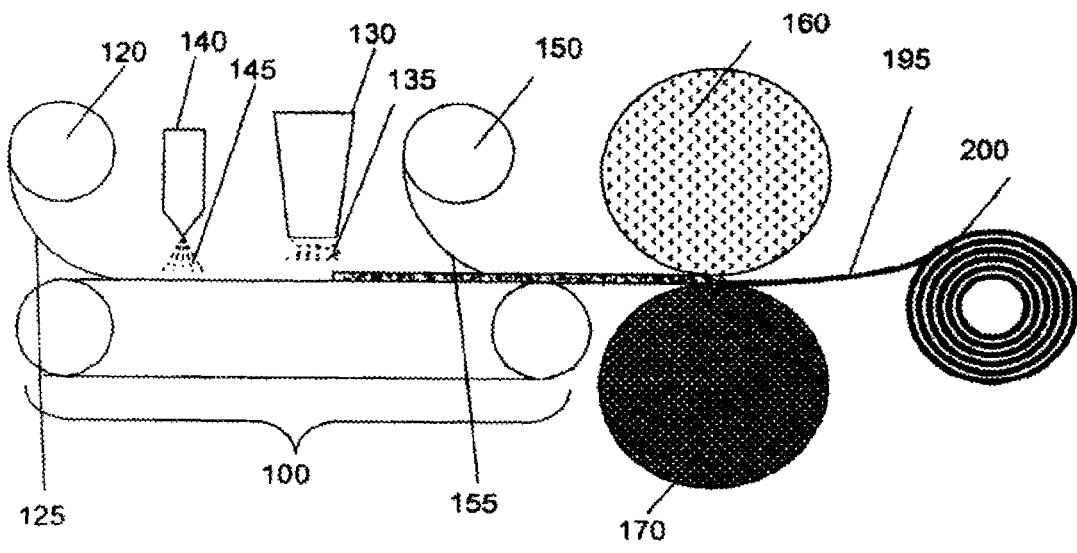
FIG. 1D is a schematic of a system for making an absorbent composite.

FIG. 1D is taken from the '598 Patent and reproduced herein, in most part, to illustrate suitable processes, subprocesses, systems, and components for making the absorbent composite and/or a disposable absorbent article incorporating the composite. Certain embodiments of the absorbent composite described herein may require modifications to the method and system illustrated by FIG. 1D. Description provided herein and/or the general knowledge in the industry will make the required modification fairly evident, however, to those skilled in the relevant manufacturing art.

Referring to FIG. 1D, a fabric 125 is dispensed from roll 120 and carried along a production line on a conveyer belt 100. The fabric 125 is a thermo plastic material that may be a woven, nonwoven, film, or a combination thereof. In some embodiments, the fabric 125 is secured to the conveyor belt 100 by a vacuum system 110. The vacuum system 110 serves to conform the fabric 125 to the convey belt 100. SAP particles 135 are then deposited on the fabric 125 by a SAP dispenser 130. The SAP dispenser 130 may be configured to position SAP particles in their desired position or lanes on the first fabric or may be configured merely to deposit SAP particles on the first fabric, whereon the SAP particles are positioned by another means. Once SAP particles have been deposited and positioned on fabric 125, a second fabric 155 introduced into the production line from roll 150 is moved into engagement with the SAP fabric 125 web. The second fabric 155 may be selected from a variety of materials including spun-bonded thermoplastic or similar woven or nonwoven material, film, or combinations thereof.

In FIG. 1D, a thermal bonding system is shown including calendar rolls 160 and 170 which are used to engage and bond fabrics 125 and 155 together. Other bonding systems may be suitable or preferred depending on the application, however. For example, an ultrasonic bonding system may be used in place of the calendar rolls to provide bond points in many applications. The bond pattern may be aligned with the distribution of the SAP particles 135. Once the fabrics are bonded to form a sheet or laminate of absorbent core composite, the sheet may be gathered into a roll 200. In other applications, depending on the composite application, the laminate may be advanced for further processing, including slitting, application of additional layers, incorporation with or into another product or even into a disposable absorbent article.

In one embodiment, the core composite has a top preferably nonwoven layer (fabric) and a bottom, preferably, nonwoven layer (fabric). The two layers may be bonded or otherwise engaged to form the pockets, as described in U.S. Pat. No. 8,148,598 B2 issued on Apr. 3, 2012, and International Application PCT/US2014/030051, both of which are commonly assigned. The '598 patent further describes a core construction employing such pockets, which is particularly suited for containing the SAP and readily and effectively disposing SAP material or SAP particles to perform the liquid absorbing or retention function, and preferably, in some embodiments, without the inclusion and employment of an absorbent matrix. In these further embodiments, the absorbent composite is characterized as being free (or lacking) of an absorbent matrix capable of stabilizing an absorbent layer of particles against particle migration and alternatively, as being pulpless. International Application PCT/US2014/030051 (the '051 application) teach further absorbent composite constructions and methods of manufacturing that advantageously secure absorbent materials beneath a cover layer, while also enhancing the fluid handling performance of the absorbent materials and\or maintaining user comfort. Accordingly, the 'disclosure of the '598 Patent and the '051 application may serve as starting points and background for the core composite constructions, absorbent articles, and manufacturing processes, and apparatus introduced herein. The '598 patent and the '051 application are hereby incorporated by reference in its entirety, and for all purposes including serving as background and reference to facilitate understanding and implementation of the products, systems, apparatus, and methods described herein.

Figures 2A, 2B, 2C, 2D:
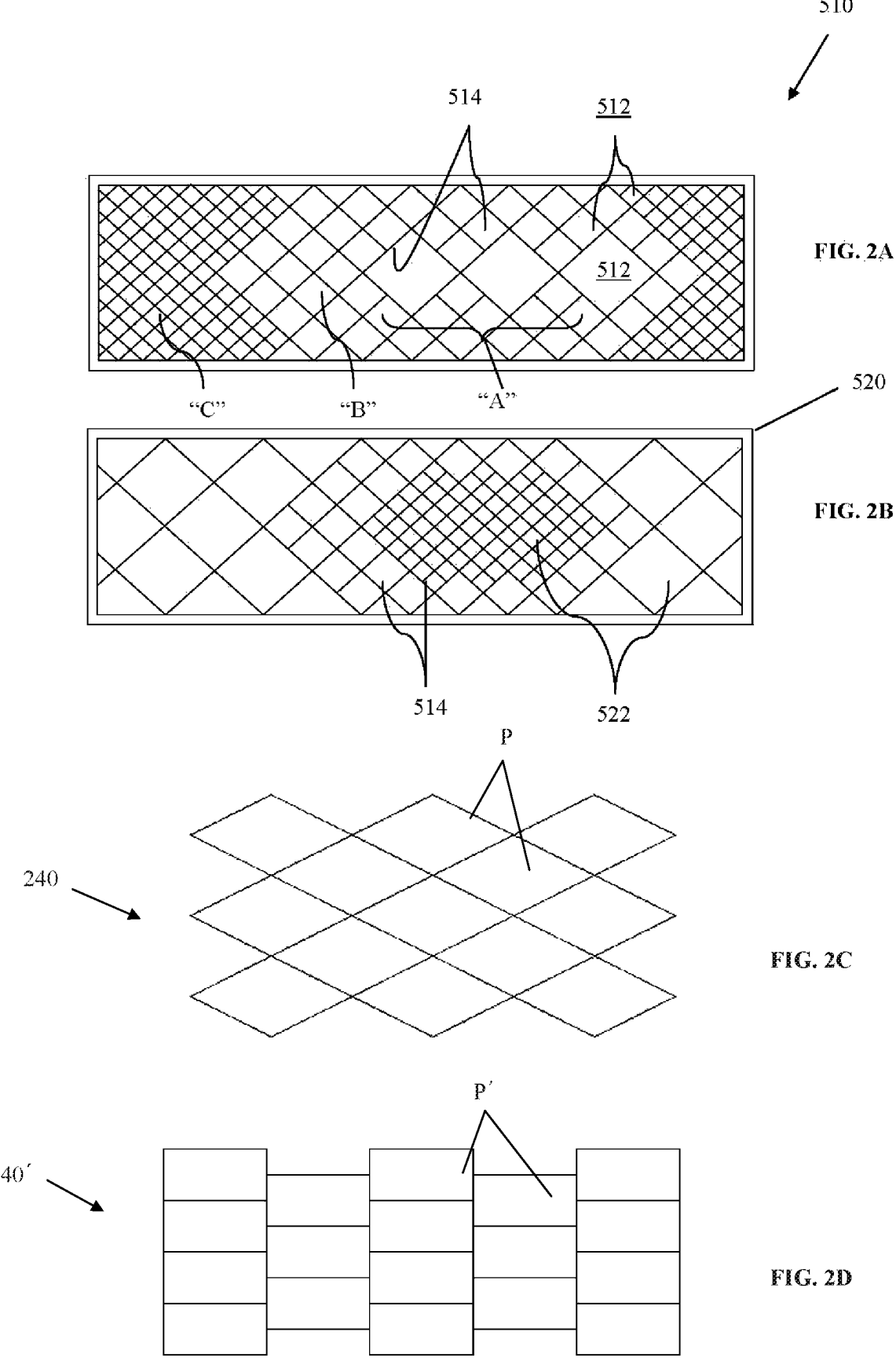
FIGS. 2A-2B is a simplified illustration of an absorbent core composite with a plurality of pockets of aggregates of absorbent particles.
FIGS. 2C-2E are bonding patterns suitable for forming pockets in the absorbent core composite such as those in FIGS. 2A-2B.

Absorbent core composites such as that depicted in FIGS. 2A and 2B may be made with particularly advantageous arrangements of aggregates of absorbent particles, such as the SAP particles. Each of the aggregates on the absorbent composite 510 is represented by the diamond-shaped enclosure 514 in the pattern. In preferred embodiments, SAP is employed as the absorbent particles in the aggregates. Furthermore, SAP aggregates in each of FIG. 1 are preferably maintained in place and stabilized by physical entrapments or containers provided by the engagement of a first fabric disposed generally above the SAP aggregate with a second fabric disposed generally beneath the SAP aggregate. Thus, in an alternative view, the diamond units represent the outline of the containers or pockets, reflecting in particular embodiments, the engagement of the top fabric with the bottom fabric, as previously described herein. The containers or pockets are also referred to as cells, herein.

The absorbent performance of the SAP can be affected by the size and structure of the container. As SAP becomes more saturated, its permeability is reduced. Water cannot pass through the SAP particle due to the high level of water already contained within the SAP particle and eventually the SAP can completely halt the passage of further fluid through it. This is known as gel blocking. Also, as SAP becomes more saturated, it swells and its volume increases. By confining the SAP in a small container of fixed volume it is possible to restrict the swelling of the SAP and prevent it from reaching its highest saturation levels (and by consequence stop the SAP from reaching its lowest levels of permeability). The degree to which the SAP particle is restricted depends on a number of factors, including: the nature and size of the container, the size and frequency of any breaks in the container (e.g., along the side walls), the amount of SAP disposed in the container, and the amount of fluid absorbed by the SAP. Further, the performance properties of SAP are affected by its degree of saturation. Specifically, absorbent composite properties such as permeability, absorption rate, capillary pressure (arising from the void space in the composite) will vary significantly as the SAP changes from dry to fully saturated. In accordance with a method of the present disclosure, target or optimal performance of the SAP may be achieved by changing the size of the container and/or the SAP concentration so as to physically constrain the swelling of the SAP and limit the maximum saturation point of the SAP. By incorporating these physical features, preferred levels of permeability or a preferred absorption property may be achieved in target regions of the absorbent core. Thus, by playing with the two variables of pocket size and the amount of SAP in the pocket, the minimum permeability of that container or pocket may be "set". Pockets in some regions of the diaper may be prevented from gel blocking and the permeability of that region of the core may be optimized. A gradient of pocket size may also be established to obtain maximum flow and utilization of the absorbent core. This gradient will extend from the target zone to the ends or sides of the diaper.

The various arrangements of containers or pockets also promote SAP and core utilization and prevent fluid from bypassing the containers. Ideally, fluid should leak or flow from container to container as the SAP reaches the maximum level of saturation which is set either by the properties of the SAP or the volume of the pocket into which it is expanding. Applicants contemplate that, in some of the previously described composites or arrangements of pockets, there may be a tendency for fluid to leak between the pockets. That is the fluid runs rapidly along the channels formed by embossing lines and does not enter the core. Fluid also flows through the nonwoven material, although not as rapidly as on the surface but faster than SAP to SAP and through SAP. To mitigate this tendency, arrangements or patterns for the containers are preferably ones that minimize or eliminate short and direct routes (as may be established along embossing lines) of fluid flow from the core center to the side margins of the core. Specifically, embossing lines for the fluid to flow along from the center of the core to the side edge of the core. To illustrate, containers or pockets shaped as diamonds are preferred to ones formed in squares or rectangles, because the diagonal lines or channels formed by the diamond containers are longer and more circuitous. Circles are also effective if packed in a way that does not present channels that flow quickly to the edge. In more preferred arrangements, fluid flow is forced to change directions one or more times before flowing through the side of the diaper.

An absorbent core for a baby diaper or adult incontinence product is required to absorb fluid quickly, in an anatomically aligned region of the core, absorb all the fluid without leaking at the sides or ends of the product and hold on to that fluid without wetting the user's skin particularly when under pressure caused by the user's bodyweight. This is accomplished by providing regions of the core having different performance parameters defined by the size of the containers retaining the SAP, as well as the arrangement of the containers. Thus, a core may be designed to attain optimized performance characteristics by changing the size of the pocket and/or the concentration of SAP within that pocket.

In FIG. 2, large diamond shaped containers or pockets 514 of absorbent particles aggregate 522 are present in a region anatomically aligned with the point of insult. The containers then gradually reduce in size toward the sides and front and rear margins or edges of the core 510. There are three distinct regions of containers. In the crotch region "A", large diamond shaped pockets are provided. Adjacent and surrounding the crotch region is an intermediate region "B" of pockets of smaller size than those in the crotch region (A). Among other things, the smaller pockets of this intermediate region (B) present breaks in the potential fluid flow around the SAP aggregates and along embossing lines. As described previously, the presentation of such barriers to direct escape of fluid flow through the side margins prevents leakage and promote utilization of the SAP aggregates. Finally, a third region "C" of pockets is present near each of the end edges of the core 510 populated by even smaller sized pockets of SAP aggregates.

FIG. 1B illustrates a second exemplary arrangements of SAP aggregates 522 and pockets 514. In this example, small, equipped with smaller capacity initially, which will cause the liquid to travel to larger cells. It may also generate a surface topography that prevents leakage from the sides and ends of the diaper, i.e., "dams" will be created that intercept and absorb surface flow.

Although the amount of SAP applied on a core by weight is of a capacity that is theoretically sufficient to achieve a certain retention target, Applicants found through experimental observations and then, calculations, that the SAP needed more volume in the pockets. Applicants' teabag volume calculations, which are reproduced under Tables A and B below, suggest that there is insufficient volume in the pockets, collectively, to allow the SAP to fully swell, hold and contain the target 750 g of liquid. There is insufficient void space within the core to accommodate the excess volume provided by the swollen SAP population. Without more expansion room, the absorbent capacity of the SAP was reduced.

The teabag calculations suggest that a diamond shaped pocket having a side dimension of 23.5 mm has a maximum internal volume of about 2.5 cm³. This is supported by testing that further suggests that a 23.5×23.5 mm bag containing 0.25 g of SAP absorbed around 2.5-3.0 g of saline solution. The core has 84 pockets resulting in a total internal volume of only 210 cm³, which is less than a third of the volume required to hold 750 g (~746 cm³) of fluid.

TABLE A

| Quick Calculation of Pocket Volume for Pocket Designs | | | | | | |
|---|---|---|---|---|---|---|
| For Adult Product width | mm | 23.55 | 25 | 50 | 75 | 100 |
| length | mm | 23.55 | 25 | 50 | 75 | 100 |
| Volume per pocket* | mm3 | 2488 | 2977 | 23814 | 80371 | 190510 |
| | cm3 | 2.49 | 2.98 | 23.81 | 80.37 | 190.51 |
| Total core area | cm2 | 480 | 480 | 480 | 480 | 480 |
| | mm2 | 48000 | 48000 | 48000 | 48000 | 48000 |
| Approx, no. of pockets | | 86 | 76 | 19 | 8 | 4 |
| Total volume capacity | cm3 | 214 | 226 | 452 | 643 | 762 |
| Total desired retention capacity is in the region of 750 g! | | | | | | |

$$V^* = w^3(h/(\pi w)-0.142(1-10^{(-h/w)}))$$

TABLE B

| For Baby Diaper | width | mm | 25 | 50 | 75 | 100 |
|---|---|---|---|---|---|---|
| | length | mm | 25 | 50 | 75 | 100 |
| Volume per pocket | | mm3 | 2977 | 23814 | 80371 | 190510 |
| | | cm3 | 2.98 | 23.81 | 80.37 | 190.51 |
| Total core area | | cm2 | 400 | 400 | 400 | 400 |
| | | mm2 | 4000 | 4000 | 4000 | 4000 |
| Approx no of pockets | | | 64 | 16 | 7 | 4 |
| Total volume capacity | | cm3 | 191 | 381 | 563 | 762 | diamond shaped pockets 522 are disposed in the region anatomically aligned with the point of fluid insults. The pockets then gradually increase in size in regions disposed toward the sides and front and rear edges of the core. The two arrangements (in FIGS. 1A and 1B) provide alternative ways of structuring the expected flow gradient and as well, handling of the liquid insults. The absorbent composite and arrangement of pockets in FIG. 1A may provide for a center region with a larger capacity initially, but which, over time, will redistribute liquid in its void volume, or from subsequent liquid insults, to smaller adjacent pockets or cells. With the pattern of FIG. 1B, the center region may be In one aspect, the present disclosure presents different approaches to solving the above-illustrated capacity issues without compromising certain advantageous features of the core design. For example, various embodiments are described or contemplated that employ diamond-shaped pockets in a core composite configuration but with the means or capability to increase void volume or capacity during use events. The pocket configuration is substantially defined by two material layers and how these two layers are secured to one another and/or the aggregate of absorbent particles contained in the pocket. It is this pocket configuration that determine the volume of the pocket and whether it can accommodate SAP well. In certain embodiments, the pocket configuration is not fixed but dynamic. A means or mechanism is provided for altering the pocket configuration so as accommodate SAP swell, particularly when the collective swell volume of the SAP aggregate nears or exceeds the fixed initial volume of the pocket. In some embodiments, the pocket configuration is altered (e.g., responsive to SAP swell (pressure or liquid contact) to increase pocket volume or capacity and/or to allow escape of liquid or SAP from the pocket.

In further embodiments, such pockets may be strategically positioned in or around certain areas of the core to effect desired fluid flow and core absorption characteristics. In yet further embodiments, the absorbent composite may be contained or encapsulated in a single or a small number of pockets.

Multiple Layers of Core Material

In this embodiment, the absorbent core composite features a multi-layer core construction. By increasing the number of core layers and thus, the z-dimension of the core, the number of pockets in the absorbent core is increased. See e.g., FIG. 3C and FIGS. 6A-6C. As a result, the total void space available in the product is also increased (multiplied) (assuming total SAP content remains the same but SAP amount per pocket is reduced). FIGS. 6A-6C provides examples of multi-layered absorbent core composites 610*a*, 610*b*, 610*c*. The configurations for the latter two composites 610*b*, 610*c* position and favor additional core layers centrally to coincide with target insult regions, for example.

In an alternative construction, a wider core sheet is provided and then folded to produce the multiple core layers. Consequently, the total void space available in the product is also increased (multiplied). Core layers can be the full length of the absorbent core or any partial length of the absorbent core and can be stacked in any configuration including overlapping partial lengths of core.

Increase Pocket Size Dimension

In further embodiments, the core pocket dimensions are evaluated and manipulated to achieve increased void space. The thrust of these core pocket designs is based on the premise that a larger pocket provides greater void space. Generally, the volume of available void space increases exponentially as the side length of the pocket is increased. With this modification, a higher total capacity per core may be achieved without increasing the overall core size or the number of layers. Thus, in respect to the pocket configuration of FIG. 2, larger diamond shaped pockets are used, which also reduces the number of cells pockets overall.

Wider Core Sheet Folded to Multiple Core Layers.

Referring to FIGS. 7A-7B in one embodiment, a wide core composite 710 can be made (FIG. 7A) and then folded (FIG. 7B), along one or more folding lines FF running parallel to lateral side edges 720 of the composite to reduce the width of the total core composite to a narrower width. Total void space is increased, as in other designs (assuming total SAP content is the same but SAP amount per pocket is reduced). Together, the two folded portions may provide a contiguous top layer 722 to the composite. Notably, in such case the base layer effectively encapsulates the composite and functions as both a core layer and a base layer. Alternatively, in a further embodiment, a longer core is folded along one or more folding lines parallel with the longitudinal front and rear edges of the core to reduce the length of the core to a desired length.

In a method for producing a suitable folded core sheet, SAP free lanes may be provided on the sheet of the non-woven base layer as the sheet is conveyed. For example, SAP is selectively deposited on the substrate along three longitudinally-extending lanes. Adhesive applied on the sheet and/or the SAP may be used to secure the SAP in place. Alternatively, a cover layer may be applied over the SAP. The three SAP lanes are mutually spaced apart by way of two SAP-free lanes, which extend in parallel with the SAP lanes. Downstream in the manufacturing process, perhaps after a cover layer is provided over the SAP, the absorbent composite may be readily folded laterally along a natural fold line extending through the SAP-free lanes (where the composite is thinner). Before folding, the base and cover non-woven layers may also be bonded along the SAP-free lanes. Notably, for a composite configuration such as that depicted in FIG. 7, the base layer may function both as the base layer and the top cover for the resultant absorbent core composite.

Extendible or Elongatable Substrates

In some embodiments, structural mechanisms are employed which, when triggered, expand or extend the dimension of one of the layered components of the core composite or more preferably, of the pocket. With the extension of the substrate, the pocket volume is increased, primarily in the Z-direction (vertical direction). FIGS. 3 and 5 illustrate another absorbent composite (320, 520) having at least one elongatable substrate, preferably as a nonwoven cover layer. The surface of the nonwoven layer is equipped with folds, flaps, pleats, grooves, or other temporary surface breaks or deformation formed during manufacture of the composite and which disturb the otherwise flat surface. Rather than being flat or smooth, the surface is riffled or corrugated. Observed in plan view, the surface is not continuous but exhibit lines or breaks (creped, riffled or corrugated) due to folds, protrusions, grooves or depression. The surface may be stretched, however, to smooth out the surface and remove these temporary deformations or discontinuities. In doing so, the surface area is increased (i.e., a surface dimension is elongated or extended). Accordingly, in one respect, the riffles or corrugations are said to represent reserved area or elongation of the surface. For present purposes of description, the terms creped, riffling, or corrugations are used to interchangeably to mean the appearance and condition of a surface as described above, including having the capacity to smoothen, elongate, or extend to increase a surface area dimension.

The riffles or corrugations may extend in either the machine direction or cross direction, but preferably, in the machine direction due to ease of assembly. As the SAP swells, it applies pressure on the nonwoven layer placing it in tension. The resulting lateral forces causes the surface discontinuities to unfold or smooth out, as the nonwoven layer extends laterally. In this way, the volume of the pocket expands to accommodate the swell of the SAP.

In FIGS. 3A and 3B, an absorbent core pocket P is shown having an elongatable substrate in the form of a riffled or corrugated non-woven cover layer A. FIG. 3A shows the pocket P both in a pre-activated state (left side of FIG. 3A) and then in an activated or expanded state (right side of FIG. 3A) characterized by SAP swell. The composite includes a base non-woven layer or substrate B, the riffled or corrugated cover layer or substrate A, and SAP aggregates 335 situated therebetween. The surface of the cover layer provides corrugations 330 under which the SAP is situated. The total SAP amount in the pocket may be in the range of 50 gsm to 600 gsm. Defined by a series of peaks and trough, the corrugations 330 may be fine and closely packed, or may be larger and provide deeper troughs or valleys. The corrugations 330 may be well defined such that the bottom of the troughs are close to the base substrate B, such as shown in FIG. 3A. In this configuration, the corrugations 330 tend to compartmentalize SAP 335 into mini-pockets. In other configurations, the bottom troughs are spaced further from the base substrate and the SAP is largely settled below the cover layer.

As taught herein, bonding of the base nonwoven layer B and the cover layer nonwoven A can form pocket patterns such as the diamond pocket pattern 340 (with intermitted or spaced apart bond sites) on a sheet S of the absorbent composite 320 shown in FIG. 3B. The perimeter of the pocket forms a flat bonded area 342 as shown in FIG. 3A. A generally flat perimeter about the pocket P is maintained during expansion of the pocket P as shown in the expanded state of the pocket in FIG. 3A. Thus, the horizontal or lateral length of the pocket P in FIG. 3A does not actually extend because the cover layer A is fixed at the bonded area 342. Extension of the cover layer A is instead generally accommodated by expansion of the pocket P in the z-direction (depth).

The corrugations 335 in the non-woven structure of the cover layer may be pulled or tensioned to elongate the surface dimension. When triggered by expanding or swelling SAP aggregate, the pocket transforms from a rest or pre-activated configuration to an activated or expanded configuration. This is illustrated in the right portion of FIG. 3A. In the activated configuration, the nonwoven surface has expanded or elongated such that the pocket volume that it defines, at least partially, has increased to accommodate the collective swell volume of the aggregate of SAP particles. Typical or preferred elongation (extended length/original length) is greater than about 1.2. Notably, the base nonwoven substrate B remains relatively flat in this embodiment.

In exemplary embodiments of a disposable absorbent garment 310, as shown in FIG. 3E, the pockets P of absorbent composite 320 are encased between a backsheet 360 and a topsheet 350. The backsheet 360 and topsheet 350 may be bonded or otherwise secured, but their placement and configuration are such that these layers do not restrict elongation of the riffled substrate and expansion of the pockets P. Specifically, the topsheet is provided with sufficient play and/or flexibility to readily accommodate the elongation and expansion. In some applications, the topsheet and/or backsheet is bonded to the absorbent core composite throughout, e.g., employing the bonding patterns discussed above to form the pockets and also bond the topsheet and backsheet. Such a bonding pattern may restrict some elongation of the riffled substrate. In other applications, the topsheet and\or backsheet is bonded only at the periphery. This bonding technique would prove less restrictive on the lateral extension of the riffled substrate. In one preferred embodiment, the topsheet is bonded only at the periphery and along one longitudinally-extending center line. In further embodiments, an ADL layer is positioned between the topsheet and the core.

In another preferred absorbent structure as first shown in FIGS. 3C and 3D, the pocket P includes a top substrate A, a bottom substrate C, and a material layer B intermediate the top substrate and bottom substrate. Substrates A and C are preferably non-woven layers that are riffled or corrugated prior to absorbent core composite assembly. As shown, the surfaces of substrates A and C exhibit riffles or corrugations 330 and a population of SAP material 335 is provided in each of the pocket spaces above and below the intermediate layer B. In the pre-activated mode, the dry SAP 335 settle close together adjacent the intermediate layer B, asserting minimal pressure on substrates A and C. The pocket P remains in a somewhat shallow or collapsed mode, exhibiting minimal height (z-direction) and riffled surfaces. FIG. 3D illustrates the pocket P and the SAP 335 contained therein in an active or nearly saturated mode. The space beneath substrates A and C now contain SAP of larger sizes. The SAP materials have absorbed liquid to near volumetric capacity, thereby expanding mostly in the z-directions, which asserts pressure on substrates A and C and forces the layers to lengthen along the MD or X-direction. As a result, more void space is created to accommodate the expanding SAP constituency.

The intermediate layer B may also be provided as an elongatable substrate in further designs. In preferred embodiments, substrate B is an ADL-like structure, i.e., bulky and capable of distributing fluid. It is normally preferred, however, that one nonwoven layer of the composite is not elongatable. Such a fixed-length nonwoven layer is required for absorbent core composite processing and handling. Otherwise, the core composite would stretch as it is being made rather than maintain the reserved length until product use. So, for a preferred two-layer composite, only one layer is corrugated. In a preferred three-layer composite, two of the layers are typically elongatable while the middle or intermediate layer is not elongatable.

In further embodiments, the intermediate layer B is a breakable substrate and more specifically, breakable upon water contact. The intermediate layer B may be provided by a tissue layer, for example. As the pocket P takes in liquid and the SAP expands, the wetted tissue layer B breaks apart to allow SAP expansion to and from either top or bottom pocket compartments. The direction of SAP expansion (or migration) may be governed by physical restriction or pressure applied to components of the pocket, and/or the direction of liquid intake and travel. In many instances, especially for pockets situated in or about the central region of a diaper where insult is initially expected, SAP immediately beneath the cover layer A will begin to swell first and exert pressure downward to adjacent SAP particles and then the intermediate tissue layer B.

In addition to improving the capacity of the core pockets, the riffled core design produces a few side benefits. Due to the depth of the corrugations, the riffled nonwoven layer necessarily provides more nonwoven material than a flat layer. The non-woven material is absorbent and thus, the additional nonwoven material and nonwoven surface area increases the absorbency of the composite. The increased thickness of the nonwoven surface due to the depth of the corrugations also improves the absorption rate of the composite. The nonwoven surface functions as temporary storage for liquid much like a typical acquisition and distribution layer.

As compared to a plain core surface, the appearance of the corrugated structure, perhaps in combination with a desirable pocket pattern, may look aesthetically pleasing and technologically advanced (market appeal). It may also look more comfortable, which, indeed, is a side benefit of the design. The corrugated core structure should be less stiff and generally softer than traditional core designs. A diaper (or other articles) employing the absorbent core is, therefore, more comfortable to a user than a traditional diaper.

Figure 2E:
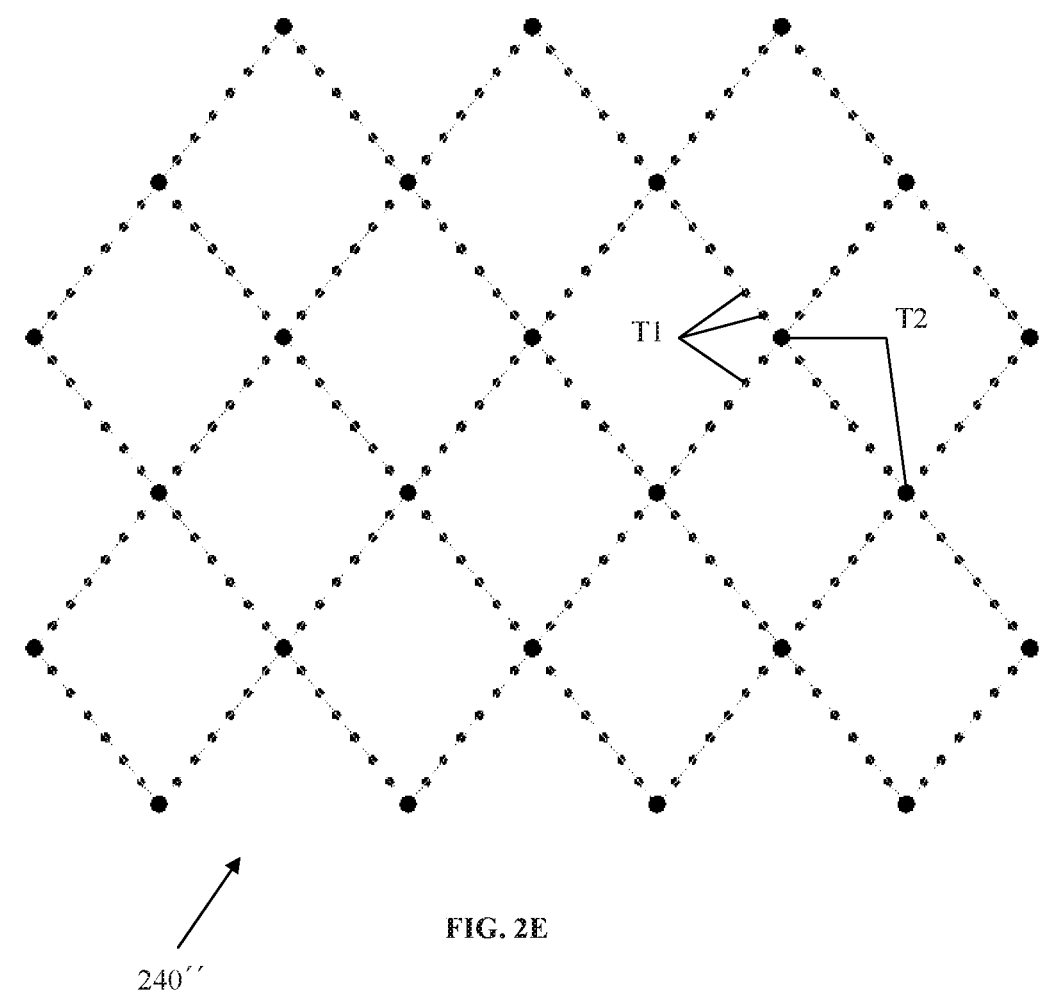

In preferred embodiments, the riffled nonwoven layer is configured such that the core is stretchable in the CD (cross) direction. See FIG. 3C. This means the corrugations and the troughs defined by the corrugations extend longitudinally or in the machine direction. This allows the pockets to continue expanding until the stretch limit of the nonwoven is reached, thereby maximizing the void volume within the core. In this regard, the cell pattern is MD-biased (machine direction biased). FIGS. 2C-2D illustrate workable or suitable cell patterns 240, 240', using diamond shaped pockets P or rectangular shaped pockets P'. FIG. 2E illustrates another diamond shaped bonding pattern 240" using intermittent bond points T1, T2. An additional benefit of CD elongatable pockets is that when the diaper is fitted to the user, stretching of the diaper around the body will cause some of the pockets to be pre-activated and elongated.

It should be noted that pockets or cells having expandable properties as described above and in further embodiments may be strategically positioned in and around different regions of the core composite. In some applications, such pockets may be provided in the central regions so as to receive directly and accommodate intake. In other applications, the core composite may be configured to readily and rapidly receive intake at the central regions and direct flow to the side regions. In such designs or configuration (but not all), it may be advantageous to locate higher volume pockets in the side regions.

FIG. 4 illustrates various methods or techniques for riffling or corrugating a sheet of the substrate A or C (forming or treating the surface so as to exhibit corrugations or riffles thereon). FIG. 4 also illustrates equipment that may be suitable for use in riffling the sheet. Referring to the illustration provided above label (a) in FIG. 4, a nonwoven sheet 400 is moved, under tension, past a comb 480 with hard, protruding fingers 482 that sharply engage and temporarily deforms the top surface of the sheet 400. This creates corrugations 430 or elongated riffles (scratching) on processed sheet 402. The dimension of the corrugations 430 will determined by the configuration of the fingers 482, as well as the basis weight and/or stiffness of the non-woven material. A thinner or more flexible nonwoven will form finer riffles or corrugations. Thicker non-woven can provide deeper corrugations and, as a result, greater elongation. Elongation may also be increased with the frequency or pitch of the corrugations. Preferably, permanent deformation (gouging, tearing, breaking, etc.) is avoided or at least minimizes, so as not to compromise the structural integrity of the material. The nonwoven sheet may be riffled before application and prior to integration in a system for making the absorbent core, or, in a system just upstream of SAP deposition. A roll of the riffled nonwoven may initially be stored on and delivered via a spool. It is conceivable, however, that in further embodiments, a nonwoven substrate is riffled in place, while it is serving as barrier to a population of SAP units.

According to another process option, illustrated and labeled as (b) in FIG. 4, the substrate 400 is placed into a engagement with a grooved roll 484 (or meshed slotted roll). The hard surface profile of the roll 484 impresses the substrate with temporary grooves into the substrate 400. The substrate 400 may be moved horizontally toward the grooved roll 484, as shown in FIG. 4, and into engagement with the hard profiled surface of the roll 484. Tension applied generally downward from and perhaps, generally perpendicularly to the horizontal direction causes the sheet 400 to turn about the grooved surface, whereby the outside surface of the roll 484 penetrates the substrate's surface. The amount of tension applied on the substrate, the angle at which the tension is applied on the moving substrate (downstream of the roller), the pitch and depth of the grooved roll's surface, and the dimensions and physical properties of the substrate, among other things, may be adjusted to achieved the desired riffled or corrugated substrate (with minimal or no permanent deformation or tearing) for use in an absorbent core composite, according to the present disclosure. In accordance with yet another process option, illustrated and labeled as (c) in FIG. 4, a pair of male and female grooved rolls 486 replaces the single roll to etch the passing substrate. As shown, the substrate 400 is passed through the interface of the two rolls 486 to produce the riffled or corrugated sheet 402.

In the preferred embodiments, only one outside surface of the substrate is corrugated and employed in the absorbent core. It is conceivable, however, that the etching process can readily etch or scratch both surfaces of the substrate. Strategic use and placement of substrates having corrugations on both sides (e.g., in and about target areas of insult) may change the fluid handling performance in those areas. Corrugations on both sides may provide additional storage capacity and\or enhance ADL-type fluid handling performance. It may provide a higher density of corrugations, if desired. Noting that a topsheet and ADL layer is typically added above the substrate, placement of the corrugations on the outside surface may not necessarily sacrifice comfort.

The simplified illustrations of FIGS. 5A and 5B depict another absorbent core composite 520 having a means for accommodating SAP swell during use. As with the absorbent core composite 320 of FIGS. 3A-3D, the absorbent composite 520 utilizes an elongatable substrate as a top nonwoven layer A over the SAP aggregate 535. The top nonwoven layer A may be activated by SAP swell to increase the volume of the pocket or cell P and accommodate the additional SAP volume. In the specific configuration illustrated, the absorbent composite 520 has the top elongatable nonwoven layer A, a base nonwoven layer B, and SAP aggregates 535 situated therebetween. Referring to FIG. 5A, bond sites 542 securing the top layer A to the base layer B mark the boundaries between SAP aggregates 535 and partly define individual pockets or cells P that contain SAP aggregates 535 thereunder. The SAP aggregates 535 and the pockets P are therefore spaced apart from adjacent SAP aggregates and pockets.

In this embodiment, the top layer A is provided with two pleats 530 or sets of double folds. The pleats 530 may be formed on the source sheet of nonwoven as the sheet is being conveyed in-line toward a web of the base nonwoven-SAP after SAP deposition. A pleat may be formed by applying a pair of opposite-facing folds on the moving sheet, as generally known in the art. In the illustrated embodiment, a pair of pleats 530 is provided for each pocket P and located to achieve the desired pocket profile when the SAP 535 swells to fill the pocket P. The folds or pleats 530 are sized to facilitate transition of the pocket P from a pre-active or thinner state to activated and full step (and other states of swell in between). It is desirable to maintain a smooth top surface and profile so as not to compromise user comfort and risk pinching of the skin by the folds or edges. In this respect, the number and size of folds and pleats may be coordinated with target swell capacity and transition performance to achieve optimal results. After applying the elongatable substrate over the SAP aggregates, the resultant composite may be passed into engagement with one or more embossing rolls to apply the desired bonding or pocket pattern.

FIG. 5B shows the absorbent composite 520 in an a state of full SAP swell and in an activated state. For each pocket P, folds or pleats are no longer evident (completely unfolded), revealing instead, a somewhat rounded top surface rather than surface discontinuities marked by sharp edges or peaks. In further embodiments, pockets with elongatable substrates (such as those illustrated in FIG. 5A or FIGS. 3A-3D) may be employed in conjunction with other means for pocket expansion or boundary breakage. For example, the pocket configuration of FIG. 3 or 5 may be employed with the breakable bond pattern of FIG. 2E. The fold pattern and the bond point sizing may be coordinated, for example, so that during use and upon liquid migration into the pocket, pressure due to SAP swell acts to elongate the top substrate first. When the volume of the pocket cannot be accommodated by pocket volume increase, certain of the bond points may be designed to break. In other designs, the absorbent core design may call for some amount of bond breakage to occur simultaneous with or preceding the elongation of the elongatable substrate.

Programmed Bond Breakage

In further embodiments, the core construction is provided with pockets having dynamic boundaries or capacities and thus, mechanisms for increasing void space. Specifically, mechanisms are established to trigger and allow for the pocket boundaries or break so as to relax the restraint on contained SAP material. Specifically, the bonds between the pockets are made to break or unzip so that the SAP can continue to swell beyond the maximum volume of the pocket. In one embodiment, discontinuities in the bond lines are provided, whereby strength of the remaining bonding strips or points are designed to be less than SAP swelling pressure.

In an alternative embodiment, the layers may be secured by ultrasonic bond sites, which may be "tuned" to a certain minimum threshold strength that may be overcome by SAP swell may overcome. Furthermore, the use of adhesive bonds, perhaps in conjunction with ultrasonic bonding, may be employed and "tuned" to provide a desired bond strength by changing and manipulating the bonding pattern. For example, lower bond strength may be achieved by smaller bond sites and higher bond strength may be achieved by larger or longer bond sites. In other embodiments, the ultrasonic bonding may serve as the stronger or permanent (or latent) bonds, whereas adhesive bond sites serve as breakable bonds or barriers. Different manners of SAP swell and pocket volume expansion may be achieved through such manipulation and bond programming.

In one application, a heated calendar roll (or ultrasonic bonding) is employed to heat, melt, and fuse the nonwoven layers at bond points. Generally, bond points below 1 mm wide break during normal use and incident of 75% (of swell capacity) SAP swell in pockets. Bond points larger than 1 mm diameter larger were observed to not break or break later. FIG. 2E illustrates a pocket pattern 240" and configuration for an absorbent composite according to an embodiment employing breakable bonds, according to the disclosure. The absorbent composite utilizes a diamond embossing pattern 240" with intermittent (spaced apart) bond points T1,T2 forming diamond shaped pocket. In this pattern, the bond points T2 located at intersections of bonding directional lines are sized to be permanent bonds while most, if not all, of the bond points T1 between the intersections are breakable. The bond points T2 at the intersections have a diameter of about 1.5 mm while intermediate bond points T1 have a diameter of about 1.0 mm (providing a bond area about half the size of the bond area at the intersections). Many of these smaller bond points T1 are expected to breach at high SAP swell states (of the adjacent pockets).

In another embodiment, water sensitive adhesive may be used in the lamination. The adhesive weakens when contacted with water and wetted, and is overcome by increasing swell pressure. Adhesives used to form a water soluble bond may employ as components, polymers that make water soluble resins, including ethylene vinyl alcohol and/or polyvinyl alcohol.

In yet another embodiment, hotmelt bonding may be employed (e.g., thermoplastic particle) to serve as the programmable, breakable bond site. In this mechanism, the hotmelt/SAP combination serves as the adhesive during manufacture and passive use of the absorbent article. When wetted, the SAP swells and weakens before breaking. As with the other proposed bonding site mechanisms, the hotmelt/SAP bond sites may be used in conjunction with one or more of the other bonding mechanism to achieve the desired breaking and pocket volume expansion effect.

Substrate Control

In some embodiments, volume expansion is effected by employing a dynamic composite layer or component. In one technique, one layer is provided by a relatively weak material that is overcome by the aggregate of SAP particles swelling beyond the pocket volume. For example, an intermediate layer, such as substrate B in FIG. 3C, may be made of tissue material that opens or is otherwise compromise by the swelling SAP aggregate, thereby expanding the void capacity. Suitable candidates for the material include drycrepe tissue, which elongates when wetted. A low wet strength tissue (e.g., low basis weight tissue) may also be selected, which weakens when wetted and is readily overcome (breaks) by SAP swell. A third material option is a slitted substrate. A fourth option is a material that has been weakened or perforated so as to be able to open up by the force exerted by the swelling SAP. In these embodiments the swollen SAP may no longer be fully contained by the material components of the core. Provision for the storage and containment of this swollen SAP would need to be made within other elements of the absorbent article. In any case, upon contact with liquid or with increasing pressure asserted by a collectively swelling aggregate of SAP, the layer opens to communicate the SAP aggregate beyond the initial fixed volume of the pocket A "tissue" is generally a (paper) cellulose-based nonwoven as opposed to a synthetic nonwoven. Preferably, the tissue is provided as a bottom or base layer of the absorbent composite, if it is intended to function as a breakable substrate. As such, it may be readily supported by a backsheet beneath it for contain liquid. In preferred designs, it would be advantageous to size and\or secure the backsheet and tissue layers so as leave expansion (containment) space beneath the tissue layer. For example, the backsheet may not be completely or tightly bonded to the core. Alternatively, a bulky nonwoven layer may be employed to provide the thicker profile.

Further Core Composite Design Considerations

In several applications wherein SAP is at least partly contained or immobilized by a fibrous network or other matrix, a procedure may be employed to facilitate the deposition of the SAP particles within the matrix. In the embodiment wherein a bulky nonwoven is used as a substrate to stabilize the SAP particles, the web carrying the SAP on the substrate may be vibrated or shaken to impart energy on the supported SAP particles. The added energy enhances the matrix' ability to capture and embed individual particles therein. In another embodiment, energy is imparted on the SAP particles by applying a vacuum to the outside of the substrate, which draws the particles toward and into the substrate. In either case, suitable equipment may be positioned immediately downstream of where SAP particles is deposited on the web of substrate.

In another embodiment, SAP of different absorption properties, i.e., absorbency under load (AUL), absorption rate or aggregate flow properties, i.e., liquid permeability, may be deposited in specific MD-stripes. For example, a stripe of approximately the same width as the length of a diaper target zone is deposited as a central zone with two stripes comprising another SAP type adjacent and abutting both sides of the first stripe. The SAP arrangement will be utilized in a CD-diaper forming process. That is, the product is formed with the longitudinal direction of the product oriented in the transverse or CD direction in the diaper converting line.

FIGS. 8A-C depict three core composition design patterns (810a, 810b, 810c) in which different grades or types of SAP material are positioned strategically to achieve desired absorption characteristics. In a technique that may be described as cross-directional (CD) profiling, certain centralized target areas or zones 822 of the core are provided with slow absorbing SAP with high absorption underload (AUL) and high permeability. In contrast, the outside areas or zones 824 are provided with slow absorbing SAP with low AUL and low permeability. The effect is that the initial intake in the central region 824 is only partially absorbed by the slow absorbing SAP with excess fluid flow being distributed to the outside regions, where it is absorbed rapidly and thus, stored. Higher performance is achieved primarily because the initial liquid insults are encouraged to spread and flow to the ends of the diaper due to the slower absorption rate or higher permeability of the first SAP which allows the liquid to flow through the target zone and into the end zones. For subsequent intakes, the central region provides yet remaining capacity to receive some or all of the additional fluid.

SAP Permeability

For present purposes, a SAP gel bed permeability greater than about 40 Darcys is considered a high permeability SAP. A permeability less than about 5 Darcys is considered a low permeability SAP. In this respect, gel bed permeability is measured under a 0.3 psi load using 0.9 percent saline solution on a 40-50 mesh particle size cut by the method described in Buchholz, F. L. and Graham, A. T., "Modern Superabsorbent Polymer Technology," John Wiley & Sons (1998). page 161. As known to one skilled in the art, the term "Darcy" is a CGS unit of permeability. One Darcy is the permeability of a solid through which one cubic centimeter of fluid, having a viscosity of one centipoise, will flow in one second through a section one centimeter thick and one square centimeter in cross-section, if the pressure difference between the two sides of the solid is one atmosphere. It turns out that permeability has the same units as area; since there is no SI unit of permeability, square meters are used. One Darcy is equal to about $0.98692 \times 10^{-12}$ $m^2$ or about $0.98692 \times 10^{-8}$ $cm^2$.

Absorbency Rates

Generally, most commercial SAPs have a vortex time ranging from 40-90 seconds. A vortex time of less than 40 would be considered a fast or high absorption rate SAP for present purposes. A vortex time of greater than 100 would be considered slow, again for present purposes. As understood by those skilled in the art, the Vortex Time Test measures the amount of time in seconds required for a predetermined mass of an absorbent polymer to close a vortex created by stirring 50 milliliters of 0.9 percent by weight sodium chloride solution at 600 revolutions per minute on a magnetic stir plate. The time it takes for the vortex to close is an indication of the free swell absorbing rate of the absorbent polymer.

AUL (Absorbency Under Load):

For present purposes, an absorbency of greater than about 15 g/g at a load of 0.09 psi would be considered high AUL. As understood by those skilled in the art, the test measures a superabsorbent's ability to absorb 0.9% saline solution against a defined pressure. Test procedures entail placing a superabsorbent a plastic cylinder that has a screen fabric as a bottom. A weight or load giving the desired pressure is put on top. The cylinder arrangement is then placed on a liquid source. The superabsorbent is soaked for one hour, and the absorption capacity is determined in g/g. See European standard EDANA ERT 442—Gravimetric Determination of Absorption under Pressure or Absorbency Under Load. See also the AUL-test found in column 12 in U.S. Pat. No. 5,601,542.

FIG. 14 illustrates, in simplified fashion, a system 1400 and process by which a sheet of an absorbent composite may be made according to the disclosure. In one respect, the system previously described of FIG. 1D may be modified to incorporate elements of the system of FIG. 14 to make an absorbent composite exhibiting SAP variations in cross machine direction. As described before, a web or sheet of a first fabric or substrate 1425 is preferably conveyed to present a planar surface. The substrate 1425 is passed beneath a SAP dispenser 1480 with means for segregating different types of SAP 1435 and depositing SAP types through apertures strategically positioned relative to the moving substrate 1425. In the illustrated embodiment, the dispensing apertures are positioned to deposit SAP at spaced apart points, which create laterally spaced apart lanes 1437 of SAP on the moving substrate 1425. Furthermore, SAP-free lanes 1439 are provided between the SAP lanes 1437.

Subsequent to SAP deposition, the second fabric 1455 is applied over the SAP-lanes creating the desired laminate. As required, the resultant laminate may be passed to a bonding area 1442 to apply the desired bonding pattern 1440 on the laminate. In an absorbent composite taken from the laminate, the SAP-free lanes between strips of SAP can act as channels for quickly directing liquid received therein.

SAP-free lanes may also be formed by providing folds in the substrate 1425 before the sheet is passed to the SAP dispenser 1480. Referring to FIG. 14, the folds may be located where the SAP-free lanes shown. In this embodiment, the SAP dispenser is selected and\or operated to apply SAP generally uniformly across the substrate 1425, including over the folds. Hotmelt adhesive is the applied over the SAP to secure it to the substrate. Thereafter, the folds may be opened (e.g., by a tenter device) to reveal the SAP-free lanes. In a further embodiment of the absorbent composite, the folds are maintained in the finished absorbent core composite rather than opened. In this way, the substrate 1425 functions as an elongatable substrate that may be activated by SAP swell during use.

Additionally, another feature that can be added in the construction described above is the addition of a small percentage of ion-exchange particles 907 to a second SAP mixture deposited in target areas, and more specifically, the end zones (outside zones 924) away from the points of insult. It has been found that the ionic strength of the urine as it passes through a bed of SAP materials (S) increases because of the SAP absorbing its water content. This is shown in the diagram of FIG. 9A, which illustrates the receipt area 922 of an absorbent core 910 for insult and the typical travel (see directional arrows) of liquid in the core 910 after initial receipt in central zone 922. The perimeter of core 910 is defined by a pair of end edges EE and a pair of side edges SE. The primary insult target 922 of the core 910

(where liquids are typically received by the core 910) is generally in and about the center of this defined perimeter. Directional arrows in FIG. 9A indicate the general advance or spread of the liquid after receipt.

The graph 901 of FIG. 9B is drawn to correspond with the expanse of the core 910 in FIG. 9A. The graph 901 illustrates the change in the liquid's ionic strength as it travels along the core 910 and the effect of this change on SAP absorbent capacity. Generally, the absorbent capacity of SAP is reduced as the ionic strength of the liquid being absorbed increases. See graph 903 of FIG. 9D. Because SAP swelling decreases with the increase in ionic strength of liquid being absorbed, SAP (S) that is furthest away from the liquid source and which contacts liquid having higher ionic strength, will have lower swelling properties.

The graph 902 of FIG. 9C illustrates the effect that the introduction of ion-exchange particles has on the SAP absorbent capacity of the same areas of the core 910. The introduction of ion exchange particles along the path of the liquid, including in these SAP areas (S) (specifically, the end zones 924) will lower the ionic strength of the liquid being absorbed there, thereby maintaining the absorption capacity of the SAP. Ion-exchange particles 907 in the fluid path restores capacity of the SAP by lowering the ionic strength of the urine reaching the ends of the core 910. So for example, a cation ion exchange resin can remove or lower the concentration of multivalent cations like Ca++ and Mg++ present in urine, hence effectively lowering the ionic strength of the urine. A typical cation exchange resin is Dow Amberlite 200C Na, used at between 1-10% of SAP content.

Accordingly, higher performance will be achieved with this construction since more liquid can be absorbed by the SAP (S) at the end zones (924).

In still another embodiment, narrow lanes that are relatively SAP-free are formed for the purpose of creating stripes used in producing diaper width strips that are bonded and sealed at the slit lines. Because several diaper widths strips can be cut from the material envisioned by this process, producing these narrower strips with sealed edges have several advantages. These include minimizing potential SAP loss during subsequent handling. This also obviates the need for a separate core wrap when assembled into a diaper.

The SAP-free lanes can also readily serve to accommodate bond lines in further processing. Additionally, these lanes can provide fold lines required of the composite design.

In another embodiment, a liquid phase/spray application of hotmelt adhesive is utilized to provide yet another form of binder or matrix to stabilize and partially immobilize SAP particles. In an extrusion process, hotmelt adhesive is forced through small holes which, in combination with air attenuation, produces elongated polymer strands or fiber. Deposited on the substrate, the elongated polymer strands establish a fibrous network capable of holding the SAP particles.

The simplified illustration of FIG. 15 provides a system 1500 that may be employed to apply the fibrous network. As before, a SAP dispenser 1580 may be used to deposit SAP 1535 on a moving fabric or substrate 1525. In the illustrated embodiment, SAP 1535 is applied uniformly across the planar surface of the substrate 1525 as it passes beneath the dispenser 1580. The SAP 1535 may be held in place, thereafter, by a variety of mechanisms, including applying suction applied to the underside of the substrate 1525, as discussed previously. Then, the substrate 1525 and SAP 1535 combination is passed beneath a hotmelt fiber extruder 1586 that dispenses and applies hotmelt fibers 1539 over the SAP 1535 and substrate 1525. The resultant composition 1510 is shown in the inset of FIG. 15.

Nonwoven Design and Selection

To achieve core performance objectives, the various core composite components may be altered or specifically designed (individually or in combination). The core performance properties of interest include absorption properties, including rate and capacity, permeability, rewet performance, and structural integrity.

The core composite typically includes a permeable top layer that receives intake and then helps contain absorbent material within the core. In one design, a nonwoven material may be selected that has an outside surface that is more open than the inside surface. The more open surface serves to readily receive SAP particles thereon, and in that respect, binds and at least partially immobilizes the SAP particles. In contrast, the opposite surface is relatively dense and advantageously more impermeable. This surface acts to block the penetration of SAP particles beyond the network of fibers presented at the more open surface. While SAP particles, particularly the smaller ones, are received and slightly encapsulated by the substrate, they are prevented from passing through the substrate. As mentioned previously, the substrate may be energized to facilitate receipt of the SAP particles by the more open surface.

The nonwoven described above is sometimes called a "bulky" nonwoven. Reference may be made to co-pending '051 patent international application for further description of suitable bulky non-woven material and selection. The "bulky" nonwoven referred to herein is, and provides, an open, fibrous network or web of hydrophilic but non-absorbent fibres. Further, as used herein, a bulky nonwovens is a fibrous web material having a thickness of between 100 μm and 10,000 μm (preferably 1,000 μm to 5,000 μm), basis weight between 15 g/m$^2$ and 200 g/m$^2$ (preferably, between 20 g/m$^2$ and 80 g/m$^2$), and density between 0.01 g/cc and 0.3 g/cc (preferably between 0.01-0.08 g/cc). Moreover, the bulky nonwoven will have an effective pore diameter between 300 μm to 2000 μm.

In further applications, it may be advantageous to employ consolidated but unbonded or lightly bonded nonwoven as one of the substrates. The unbonded surface may serve well embedding and supporting the SAP particles. The outside may be bonded, however, so as to maintain structural integrity and impermeability. In further applications, the unbonded surface may be bonded after application of SAP particles thereon by using hotmelt or infrared heating. This procedure may be necessary or advantageous, as it imparts structural integrity to the composite's nonwoven layer. Although an already bonded nonwoven layer may have been used, the bonding in place technique allows for the SAP particles to be bonded and supported also, in one bonding operation. By using hotmelt or IR to bond the nonwoven (with SAP) after application of SAP, the nature of SAP encapsulation and hence the composite integrity, swelling properties and fluid flow or permeability characteristics can be varied and controlled.

In specific embodiments, suitable bulky/high loft materials contemplated for use in the above suggested applications are a type of "through air bonded" nonwovens. The nonwovens are made by taking a carded web or mat of fibers and using hot air to bond the fibers at the points where the fibers intersect or join. The hot air "blowing" through the web serves to keep the fibers separated to some extent and uncompacted. The resultant structure is, therefore, fairly open but fixed by bonds formed between the intersecting fibers. (This is different from the traditional process by which non-bulky, regular nonwovens are made, wherein an unbonded mat of fibers is passed through heated bonding rolls that compact the fibers and form a thin web of non-woven, and leave an embossed bonding pattern). In an exemplary method of manufacturing the absorbent compos-ite, a web of carded, unbonded fibers (e.g., PET fibers) is conveyed and SAP is deposited on the web. Hot air or other suitable means is then used to bond the SAP and the non-woven in place.

Hotmelt Application Design and Selection

As described previously, in one embodiment, a liquid phase/spray application of hotmelt adhesive is utilized to provide yet another form of binder or matrix to stabilize and partially immobilize SAP particles. In an extrusion process, hotmelt adhesive is forced through small holes which, in combination with air attenuation, produces elongated poly-mer strands or fibers. Deposited on the substrate, the elon-gated polymer strands establish a fibrous network with capacity to hold the SAP particles.

In an alternate method, powdered hotmelt adhesive par-ticles can be mixed with superabsorbent particles and the mixture of unbonded hotmelt particles and superabsorbent particles is applied to the nonwoven substrate. Application of heat to the composite will cause the hotmelt adhesive powder to melt and bind the SAP and nonwoven substrate. The application of heat can be accomplished through IR (infra-red) radiation methods, heated calendar rolls or other means.

The selection of hotmelt material and processes as a design element can achieve particularly improved product performance. In further applications, the ratio of hotmelt particles to superabsorbent particles is selected to achieve an optimum balance of dry integrity and restraint on SAP swelling. The ratio of the number of SAP particles to hotmelt particles will determine for example, how many bonding points, contributed by the hotmelt particles, per SAP particle are possible. The ratio is determined from the weight per-centage, particle size distribution and polymer density of each component. For example:

| hotmelt particle size range: | 0-120 u | 0-200 u | 0-300 u |
|---|---|---|---|
| particle ratio (HM to SAP): | 46.79 | 27.06 | 9.75 |
| optimum adhesive content: | 2.1% | 3.7% | 10.3% |

Here, optimum adhesive content is defined as one particle of hotmelt per particle of SAP and uniform mixing is assumed. The ratios shown are for commercially available SAP and hotmelt particles. The chart of FIG. 9 provides particle size distribution for a SAP material SAP (W-112 from Nippon Shokubai). The hotmelt particles are commer-cially available materials from Abifor and have the follow-ing particle size distribution provided in FIG. 10. The hotmelt to SAP weight ratio can range from 1%-30% of SAP content, preferably from 4% 12%.

The selection of hotmelt material and processes as a design element can achieve particularly improved product performance. In some applications, water sensitive hotmelt particles may be employed as a mechanism for increasing void space (swell volume). Specifically, a hotmelt is selected that is sensitive to wetting (e.g., an SAP based hotmelt) and thus, to receipt of liquid intake in the absorbent core pockets. These hotmelt particles break down as the SAP particles around it swell with liquid absorption. This relieves the SAP particles from the hotmelt's bind and allow the SAP to swell unrestricted. An example of a water soluble hotmelt is the modified polyvinyl alcohol resin (Gohsenx L series, Nippon Gohsei). An example of a water sensitive hotmelt is Hydro-lock (HB Fuller).

SAP Selection and SAP Aggregate Constitution

As described previously, the pockets of SAP aggregate need not be uniformly provided or distributed across the core composite. Variations in pocket size and shape, pocket volume, SAP volume, SAP-pocket volume ratio, and SAP concentration may be manipulated to achieve performance objectives. In addition to those design parameters, the dis-tributions or constituents of the pockets, including the SAP aggregate, may be varied as design elements.

In various embodiments, absorbent composite design takes into account the size and distribution of the SAP particles. As general guiding principles, the permeability of a SAP assembly increases linearly with particles sizes (large SAP particle sizes have highest permeability). For example, doubling the particle size will double the permeability of the SAP assembly. Further, the permeability of a SAP assembly decreases with loading or swelling restraint (effect seen with small pockets). Finally, permeability decreases with increas-ing saturation (after initial 25% saturation).

In one embodiment, the SAP aggregate constitution may be selected to include a certain mix of smaller particles that penetrate the surface of the nonwoven layer and larger particles that generally remain above the nonwoven surface. The nonwoven surface may also be prepared or preselected based at least partially on the desired particle filtration effects. The result is a layering of the SAP particles at the interface of the non-woven and the SAP (see e.g. absorbent composite 1110 of FIG. 11). Such layering and separation of SAP particles can be utilized to change the fluid uptake behavior of the segregated layers formed. The layer formed from the larger particles will have a higher permeability relative to the layer formed from the smaller particles. Such an arrangement can encourage the lateral flow of liquid during the insult resulting in more fluid distribution and spreading. To aid the filtration technique, the nonwoven may be energized during the manufacturing process to impart and encourage particle separation in the SAP.

In methods of manufacturing the preferred composite, the multi-layer core substrate may be pre-fabricated by a sup-plier according to specification. Suitable "through-air bonded non-wovens" may be made in a single process by combing PP/PE/PET fibers into a web and then bonding the web by blowing hot air through the non-woven. As a result, thermal bonds form between the crossing fibers. As gener-ally known in the art, multi-layer to structures may be made by combing different layers of nonwoven on top of each. For example, three combs may be provided to build up three different layers of nonwoven, each layer having a different combination of fibers, density, and thickness. Preferably, a roll of the prefabricated multi-layer substrate is conveyed onto a manufacturing line whereupon a SAP mixture is deposited on the moving core substrate.

In the alternative, the multi-layer core substrate may be made on-site and further, on-line. For example, three sepa-rate rolls or sheets of high loft nonwovens may be delivered (e.g., unwound) and combined into a multi layer web. The layers may be bonded by applying a layer of hotmelt adhesive between each layer of nonwoven (e.g., applied by spray or slot hotmelt coater). Alternatively, the nonwoven layers may be point or line bonded by applying heated engraved/patterned calendar roll onto the web. An ultrasonic bonding method may also be employed. In any case, thermal or ultrasonic bonding may be performed before or after depositing SAP onto the multi-layer core substrate.

To reduce cost and process complexity, each of the SAP intended for each layer is joined with and delivered onto the multi-layer substrate simultaneous with the other SAP constituents. SAP grades are selected having the desired particle sizes and ranges. The arrangement of different density nonwovens will act to separate and place the SAP particles in the appropriate layers. It is contemplated, however, that certain applications may require separate and independent deposition of the different SAP populations directly onto the intended core substrate layer. In one example, the smallest SAP particles are applied directly onto highest density layer, the medium size particles applied to the intermediate layer, and largest particles applied to the lowest (and top/bodyside) density layer. In a more specific example, the bottom nonwoven layer is first conveyed and then deposited with the supply of small SAP particles. Then, the intermediate layer is applied over the first nonwoven layer followed by deposition of medium size SAP particles directly onto the exposed surface of the intermediate layer. The top nonwoven layer is then applied over the SAP-saturated intermediate layer, followed by larger particle size SAP being deposited directly onto the top nonwoven layer.

In certain embodiments, a disposable absorbent article incorporating the absorbent core composite will include a topsheet and backsheet. The core composite is sandwiched between the topsheet and backsheet, with the topsheet providing the bodyside liner or cover. In further embodiments, the bodyside material layer of the core composite functions as the topsheet, thereby eliminating the need for the topsheet.

For purposes of this description, low, medium, and high density nonwovens are nonwoven materials having a density of 0.01 to 0.03 g/cc, 0.03 to 0.08 g/cc, and 0.09 to 0.12 g/cc, respectively. The preferred thickness of the low, medium, and high density nonwoven layers is 1.5 mm to 5 mm, 0.6 to 3 mm, and 0.15 to 0.6 mm, respectively. The specification depends on the basis weight and density of the nonwoven, as shown in Table 1 below. Table 1 below may be referred to in selecting suitable low, medium, and high density nonwovens to satisfy absorbent composite design requirements. Moreover, preferred nonwovens will be commercially available multi-layer webs of different fiber denier and density for each layer, typically using carding technology with multiple formers. An example of such a suitable web would be a double or triple layer structure typically used as an ADL (acquisition-distribution layer) available from Libeltex Nonwovens, Belgium, (Dry Web TDL2, Slim Core TL1, TL4, TL5).

TABLE 1

| | | Web Thickness (in microns) vs. Basis Weight and Density | | | | | | | | | | | | |
|---|---|---|---|---|---|---|---|---|---|---|---|---|---|---|
| | | Web Density | | | | | | | | | | | | |
| | | 0.01 | 0.02 | 0.03 | 0.04 | 0.05 | 0.06 | 0.07 | 0.08 | 0.09 | 0.1 | 0.12 | 0.2 | 0.3 |
| Basis Weight | 15 | 1500 | 750 | 500 | 375 | 300 | 250 | 214 | 188 | 167 | 150 | 125 | 75 | 50 |
| | 20 | 2000 | 1000 | 667 | 500 | 400 | 333 | 286 | 250 | 222 | 200 | 167 | 100 | 67 |
| | 30 | 3000 | 1500 | 1000 | 750 | 600 | 500 | 429 | 375 | 333 | 300 | 250 | 150 | 100 |
| | 40 | 4000 | 2000 | 1333 | 1000 | 800 | 667 | 571 | 500 | 444 | 400 | 333 | 200 | 133 |
| | 50 | 5000 | 2500 | 1667 | 1250 | 1000 | 833 | 714 | 625 | 556 | 500 | 417 | 250 | 167 |
| | 60 | 6000 | 3000 | 2000 | 1500 | 1200 | 1000 | 857 | 750 | 667 | 600 | 500 | 300 | 200 |
| | 70 | 7000 | 3500 | 2333 | 1750 | 1400 | 1167 | 1000 | 875 | 778 | 700 | 583 | 350 | 233 |
| | 80 | 8000 | 4000 | 2667 | 2000 | 1600 | 1333 | 1143 | 1000 | 889 | 800 | 667 | 400 | 267 |
| | 90 | 9000 | 4500 | 3000 | 2250 | 1800 | 1500 | 1286 | 1125 | 1000 | 900 | 750 | 450 | 300 |
| | 100 | 10000 | 5000 | 3333 | 2500 | 2000 | 1667 | 1429 | 1250 | 1111 | 1000 | 833 | 500 | 333 |
| | 110 | 11000 | 5500 | 3667 | 2750 | 2200 | 1833 | 1571 | 1375 | 1222 | 1100 | 917 | 550 | 367 |
| | 120 | 12000 | 6000 | 4000 | 3000 | 2400 | 2000 | 1714 | 1500 | 1333 | 1200 | 1000 | 600 | 400 |
| | 130 | 13000 | 6500 | 4333 | 3250 | 2600 | 2167 | 1857 | 1625 | 1444 | 1300 | 1083 | 650 | 433 |
| | 140 | 14000 | 7000 | 4667 | 3500 | 2800 | 2333 | 2000 | 1750 | 1556 | 1400 | 1167 | 700 | 467 |
| | 150 | 15000 | 7500 | 5000 | 3750 | 3000 | 2500 | 2143 | 1875 | 1667 | 1500 | 1250 | 750 | 500 |
| | 160 | 16000 | 8000 | 5333 | 4000 | 3200 | 2667 | 2286 | 2000 | 1778 | 1600 | 1333 | 800 | 533 |
| | 170 | 17000 | 8500 | 5667 | 4250 | 3400 | 2833 | 2429 | 2125 | 1889 | 1700 | 1417 | 850 | 567 |
| | 180 | 18000 | 9000 | 6000 | 4500 | 3600 | 3000 | 2571 | 2250 | 2000 | 1800 | 1500 | 900 | 600 |
| | 190 | 19000 | 9500 | 6333 | 4750 | 3800 | 3167 | 2714 | 2375 | 2111 | 1900 | 1583 | 950 | 633 |
| | 200 | 20000 | 10000 | 6667 | 5000 | 4000 | 3333 | 2857 | 2500 | 2222 | 2000 | 1667 | 1000 | 667 |

A typical core composite will be provided with SAP in the range of about 100 gsm to 500 gsm. Of this amount, about 5% to 75% may be in one single layer of the absorbent composite. The highest density layer may have as little as about 0.5% to 5% of the total SAP amount. It should be noted that some SAP may not penetrate onto the nonwoven layers at all, but sit on the outside surface. In exemplary two layer constructions, the average size dimension of SAP particles (i.e., width or diameter) targeted for a first or high density layer (and which, will generally pass through a nonwoven layer above it) is 0-300 microns. The second or lower density layer will contain larger sized particles, including so-called medium size and large size SAP particles typically in the 300-850 microns range. In a three layer composite, the large SAP particles, which are expected to not penetrate the intermediate layer, will be retained in the top or lower density nonwoven layer and have an average size dimension greater than 600 microns (in the 600-850 microns range), and the medium size SAP particles will be in the range of 300 to 600 microns (in the intermediate density nonwoven layer). Accordingly, the smaller size particles will be in the range of 0 to 300 microns (in the high density nonwoven layer).

FIG. 11 provides, in elevated cross-sectional view, an absorbent composite 1110 having a multi-layer configuration discussed above. A high density nonwoven serves as the base layer NW1 and is shown containing a representative population small SAP particles. An intermediate layer NW2 is provided by a medium density nonwoven and contains a representative population of medium size SAP particles S2. Finally, atop the intermediate layer NW2, a low density, open nonwoven provides a top layer NW3, which, as incorporated into a disposable absorbent particle is situated bodyside (closest of the composite's layers to the user's skin) and likely adjacent a topsheet.

In some embodiments, the SAP particles penetrate well into the multi-layer composite and may be bonded therein (e.g., by application of hotmelt particles, spray hotmelt, etc.). No additional cover layers are required. In making the disposable absorbent article, a topsheet is applied directly over the multi-layer composite. In other embodiments, an additional nonwoven layer or even tissue is applied as a cover layer over the composite to further secure the SAP. Alternatively, the additional nonwoven or tissue may be wrapped all the way around (enveloping) the multilayer composite construction. In another alternative embodiment, hotmelt fibers is sprayed over the top surface of the multi-layer construction maintain the SAP in place.

It should be noted that particle size determination as alluded to above, and in the selection of such particles in a corresponding design or method, is largely implemented by equipment operated to dispense the SAP. In suitable applications, a sieve will be provided with the appropriate screen or mesh. The screen or mesh will be specific to the size of SAP particles being separated. Furthermore, the separation and\or mixing of SAP particles may be partly or entirely performed in process, preceding to or in conjunction with SAP deposition, or prior to the manufacturing process.

An absorbent core composite sheet providing an absorbent construction according to the above description and FIG. 11 may, subsequent to SAP deposition and securement, be bonded to further secure the SAP. As described above, a bonding pattern applied to the sheet creates pockets of SAP aggregates. For example, a diamond embossing pattern as described previously in respect to FIG. 2 may be employed to bond the outside nonwoven layers. In alternative embodiments, the composite sheet may be slit and cut longitudinally to produce multiple core composites or sheets. In such an application, the source core sheet for slitting may be delivered with uniform thickness and without pockets.

When utilizing hotmelt particles as binder for SAP preserving aggregates, the SAP particle size and quantity relative to hotmelt particles may be a design consideration for improving or preserving SAP performance. Generally, the amount of hotmelt particles must be adequate for binding the SAP. Excess hotmelt particles or material may, however, work to reduce capacity and absorption rate of the SAP particle. This is due to the hotmelt material possibly coating or blocking the SAP particle, and as well, restricting movement and swelling. In preferred embodiments, the ratio of hotmelt particles to SAP particles is one-to-one.

In further embodiments, the SAP aggregate constitution may include a combination of SAP particles, in the spherical and/or flake forms, and SAP in the superabsorbent fiber form (sometimes referred to as SAF). Specific combinations and ratios may be selected to achieve desired fluid or absorbent properties, as well as structural properties. For example, in embodiments wherein a bulky layer is employed with a combination of spherical SAP and superabsorbent fibers, smaller spherical SAP will gravitate to and penetrate the open fibrous surface of the bulky nonwoven. In contrast, the superabsorbent fibers will tend to settle atop the surface.

In another embodiment, the SAP aggregate constitution is populated or rather, infiltrated, by smaller inert particles which position themselves between the larger SAP particles. This increased spacing increases the permeability of the SAP aggregate. The void volume available within the aggregate is increased due to the spacing. As a result, the SAP particles located inside the aggregate are less likely to experience gel blocking. Preferably, the spacing particles are inert so as not to alter the SAP properties, and sufficiently small so as not to significantly increase the volume of the aggregate, the pocket, or core composite.

An example of a suitable inert particle is an ion exchange resin particles (as also described previously). In this mode, it can be distributed throughout the absorbent composite, including sections intended as target area. As described previously, the addition of ion exchange particles will serve to increase the capacity of the SAP at the target zone and throughout the core because it will reduce the ionic strength of the incoming fluid (urine). Typical ion exchange resin particle size used in these applications will be about 300-400 microns in size. Another suitable, and readily available, source of a spacing particle are microporous silica gel beads. Silica gel is an amorphous form of silicon dioxide that is synthetically produced in the form of hard regular beads. It has a microporous structure and is typically used as a high capacity desiccant. The gel beads are available in suitable particle sizes between 150 microns-2000 microns or greater. In addition to functioning as a spacer, the silica gel can also be used as a carrier for other ingredients such as fragrances and odor control agents. These ingredients are pre-applied to the microporous beads and will be contained within the bead when deposited with the SAP.

To illustrate, FIG. 12 provides a general depiction of the distribution and mutual spacing of SAP particles S as found in an absorbent core composite, with and without the aid of inert particles (ii). On the left portion of FIG. 12, a normal distribution of the SAP particles (S) are shown relatively firmly packed in a given volume or area. Then, a joint population of inert particles (ii) and SAP (S) is introduced into the same area or volume. As shown on the right side of FIG. 12, the inert particles (ii) situate themselves between SAP particles (S). As a result, the spacing between SAP particles is increased, even with inert particles randomly occupying some of the space. There are less SAP particles (S) in the same area. In FIG. 12, the average dimension (i.e., diameter) of the inert particles is less than about 40% of that of the SAP particle (for illustration). It should be noted however, that FIG. 12, shows only the area. The actual space between SAP particles is in three dimension and thus, the increase in volume (not area) between SAP particles (with the inert particles (ii) is greater (one degree of order higher than area calculation).

In a further embodiment, the SAP aggregate constitution may include a water-soluble particle to perform the spacing function. The spacing particle in this constitution will, however, dissolve upon liquid intake. This serves to provide yet additional void volume, and to accommodate SAP swell. An example of a suitable source of water-soluble particle is a polyvinyl alcohol. A low molecular weight, cold water soluble PVOH may be used (i.e., Selvol 203 (Sekisui SC), Poval PVA-203 (Kuraray)).

In a yet another embodiment, wherein a hotmelt adhesive is employed, heat sensitive, volatile particles are employed as spacers or spacing particles. When a bonding step applies heat to activate the hotmelt, the spacer particle evaporates leaving the SAP, the hotmelt particles, and additional void space between SAP particles (see FIG. 13). Selection of suitable volatile particle must, of course, take into consideration possible safety and practical concerns, including the level of energy required to activate the material. The material is incorporated material in solid form to the SAP mixture for deposition and then vaporizes upon the application of heat or vacuum. Possible sources are dry ice and iodine.

FIG. 13 provides a graphical chart 1300 that illustrates the various mechanisms described above, and the interactions between SAP aggregate constituents. Each of four rows or panels of the chart 1300 illustrate the packing (i.e. spacing and distribution) of SAP particles and non-absorbent particles, including spacing particles, in a representative portion of the absorbent composite. The top row (a) relates to the addition of hotmelt particle to the SAP population. Before bonding, the hotmelt particles occupies a small space between SAP particles. During bonding, the hotmelt particle melts, leaving space between SAP particles. As illustrated by the right most frame, SAP later swells to fill up much of the space between SAP particles. The next row (b) illustrates particle packing when inert particles is added—to the mix of hotmelt particle and SAP. As shown in the first frame, the inert particles help to space the mutually space SAP, even after the hotmelt transforms to a coating after bonding. Later, when a SAP particle begin to swell, it can expand into the void left by the hotmelt particle.

The next row (c) illustrates the addition of volatile particles to the mix of hotmelt and SAP. The volatile particles help to mutually space the SAP particles and increase permeability. As shown in the rightmost frame, the inert particles continues to help space the SAP from each other, even during product use and SAP swell. FIG. 13 depicts, in the last row (d), the addition of water soluble particles into the SAP-hotmelt mix. The water soluble particles remain in the mixture even when the hotmelt particle disappears after bonding. The water soluble particles dissolve, however, in use, as the pocket begins to takes on water content. As shown to the right of FIG. 13, SAP occupies volume between SAP particles and helps to space the particles, but gives up this space to expanding SAP particles during use.

Each of the schematics of FIGS. 16 and 17 illustrates an exemplary system (1600, 1700) and method for making an absorbent core composite according to one or more of the embodiments described above. In a method according to FIG. 17, a sheet or fabric 1625 is dispensed from spool 1620 and carried along a production line on a conveyer belt 1605. The sheet or fabric provides the substrate 1620 of the finished absorbent core composite. In various preferred embodiments, the substrate 1625 is nonwoven thermo plastic material. The sheet 1625 is subjected to a riffling or corrugating process by which one surface of the sheet is etched or scratched to produce riffles or corrugations thereon, as previously discussed in respect to FIG. 4. In this example, a pair of grooved rolls 1686 (one female and one male) is employed to create the desired corrugation dimensions and pitch. The corrugations are directed in the machine direction. Adhesive is then applied on the corrugated surface in preparation for and as required of SAP to be deposited on the surface (see adhesive applicator 1688) In this embodiment, two SAP dispensers 1680a,1680b are employed serially deposit SAP on the riffled or corrugated surface. The first dispenser 1680a operates to deposit SAP almost all the way across the moving substrate. The second SAP dispenser 1680b operates to deposit SAP onto a central region of the substrate, thereby supplementing the SAP amounts previously deposited in that region. For some absorbent composite designs wherein SAP amounts vary in the longitudinal direction, the second SAP dispenser 1680b may be operated intermittently. See, for example, the core designs of FIG. 6 and the accompanying description. The second SAP deposited may also be of a type different from the first SAP deposited, and\or contain a constitution different from the first deposit (e.g., contain non-SAP materials not provided with the first SAP). The second SAP may, for example, exhibit properties particularly advantageous for use in the central region of the finished core. In this embodiment, the SAP is secured on the sheet 1625 and the sheet 1625 is secured to the conveyor belt 1605 by a vacuum system applying suction to the sheet 1625.

Referring again to FIG. 16, a second sheet or fabric 1625 is simultaneously dispensed from a second supply spool and carried along a production line on a second conveyer belt 1607. In various embodiments, the second fabric 1655 is a nonwoven material that provides the top substrate or cover layer for the absorbent core composite. In this embodiment, the top substrate is also elongatable. Accordingly, the second sheet 1655 is also subjected to a riffling or corrugating process. Thereafter, adhesive may be applied to the riffled or corrugated surface, before the sheet meets the main production line 1605 and engages the now SAP-lined first sheet 1625. At this juncture, a three-layered composite is formed and advanced on the production line. In the embodiment shown, the composite is passed between a pair of embossing rollers 1660 to apply a desired bonding pattern on the composite and form pockets of SAP aggregates. The resultant absorbent composite may, therefore, feature a plurality of spaced-apart pockets having a top and bottom elongatable substrates. The pockets in the central region may fuller and contain more SAP than pockets located to the side of the central region.

FIG. 17 illustrates a further variation of the system and method illustrated by FIG. 16 (wherein like reference numerals are used to indicate like elements). Like the absorbent composite described in respect to FIG. 16, the absorbent composite made by this system 1700 and process provides a plurality of pockets of SAP aggregate having an elongatable top layer and an elongatable bottom layer. The absorbent composite employs, however, a third or intermediate layer that is not elongatable. The intermediate layer may be provided by tissue material, which is considered breakable when wetted. Such an absorbent composite constructions is illustrated by FIG. 3C. As shown in FIG. 18, a third substrate 1765 is applied intermediate the two sheet 1725, 1735 and more specifically over the SAP-lined first sheet. SAP is then deposited on the non-corrugated surface of the intermediate sheet 1765 before the third sheet 1755 is applied over the then SAP-lined intermediate sheet 1765. After engaging embossing rollers 1760 for bonding, the resultant absorbent composite features a plurality of spaced apart pockets of SAP aggregate, wherein the three-layered pocket is made expandable top and bottom nonwoven substrates.

It is noted that in the various exemplary descriptions provide above, there are occasional mention of a corresponding steps or processes in making the core composite (or disposable absorbent article). Although the description may not necessarily be provided from the perspective of manufacturing product, it is believed that various manufacturing or core preparation methodologies, and equipment associated therewith, will become apparent from a reading of the various descriptions, perhaps in conjunction with common knowledge in the art or the references cited herewith.

The foregoing description has been presented for purposes of illustration and description of preferred embodiments. This description is not intended to limit associated concepts to the various systems, apparatus, structures, and methods specifically described herein. For example, the various pocket designs may be employed in various types of disposable absorbent articles. Moreover, the various mechanisms of increasing void space or volume may be used in different combination, and at varying degrees, as required for the absorbency demands of a product. The embodiments described and illustrated herein are further intended to explain the best and preferred modes for practicing the system and methods, and to enable others skilled in the art to utilize same and other embodiments and with various modifications required by the particular applications or uses of the present invention.

What is claimed is:

1. A method of making an absorbent composite for incorporation into a disposable absorbent garment, said method comprising:

deforming a surface of a first sheet of a first nonwoven layer to form laterally elongatable surface discontinuities;

conveying the first sheet of the first nonwoven layer;

wherein said deforming of the surface is performed prior to said conveying said first sheet;

combining the first sheet with a second sheet of a second nonwoven layer;

positioning absorbent particles between the first and second sheets, thereby forming a composite including said first and second sheets sandwiching said absorbent particles therebetween;

wherein said positioning of the absorbent particles includes depositing the absorbent particles on said first sheet;

wherein said combining the first and second sheets includes applying the second sheet of the second nonwoven layer over the deposited absorbent particles and first sheet, thereby forming the composite including said first and second sheets sandwiching the absorbent particles therebetween;

bonding said first and second sheets to secure, at least partially, said absorbent particles therebetween;

wherein said surface discontinuities are at least partially removed in an expanded configuration such that said first sheet is at least partially laterally elongated in said expanded configuration.

2. A method of making an absorbent composite for incorporation into a disposable absorbent garment, said method comprising:

conveying a first sheet of a first nonwoven layer;

prior to said conveying said first sheet, deforming a surface of said first sheet to form laterally elongatable surface discontinuities;

depositing absorbent particles on said first sheet;

applying a second sheet of a second nonwoven layer over the deposited absorbent particles and first sheet, thereby forming a composite including said two material layers sandwiching absorbent particles therebetween; and bonding said first and second sheets to secure, at least partially, said absorbent particles therebetween;

wherein said deforming comprises folding one or more sections of said surface of said first sheet to form laterally elongatable folds thereon, providing folded sections in said first sheet; and wherein, after applying said second sheet, unfolding said folded sections to reveal lanes free of absorbent particles.

3. The method of claim 1, wherein said deforming the surface of said first sheet comprises corrugating the first sheet.

4. The method of claim 1, wherein, after said deforming the surface of said first sheet, the first sheet is creped.

5. The method of claim 1, wherein, after said deforming the surface of said first sheet, the first sheet comprises protrusions.

6. The method of claim 1, wherein, after said deforming the surface of said first sheet, the first sheet comprises grooves.

7. The method of claim 1, wherein, after said deforming the surface of said first sheet, the first sheet comprises depressions.

8. The method of claim 1, wherein said bonding the first and second sheets comprises forming bond sites between the first and second sheets including forming breakable bond sites and permanent bond sites.

9. The method of claim 8, wherein said breakable bond sites comprise adhesive bonds and said permanent bond sites comprise ultrasonic bonds.

10. The method of claim 9, wherein said adhesive bonds comprise water sensitive adhesive.

11. The method of claim 9, wherein said adhesive bonds are smaller than said permanent bonds.

12. The method of claim 8, wherein said bond sites are spaced apart bond sites.

13. The method of claim 1, wherein said bonding forms pockets between the first and second sheets, and wherein said absorbent material is positioned within said pockets.

14. The method of claim 13, wherein each said pocket has an initial configuration with a fixed initial volume that contains an aggregate of said absorbent material in a dry state, and wherein each pocket, in the expanded configuration, accommodates a swell volume of said aggregate associated with a liquid saturation state.

15. The method of claim 1, wherein said absorbent particles comprise SAP particles.

16. The method of claim 1, wherein said deforming the surface of said first sheet comprises riffling said first sheet.

17. The method of claim 1, wherein said deforming the surface of said first sheet comprises forming pleats in said first sheet.

18. The method of claim 1, wherein said deforming the surface of said first sheet comprises forming a plurality of folds in said first sheet.

19. The method of claim 2, wherein said absorbent particles comprise SAP particles.

* * * * *